United States Patent
Balkin et al.

(10) Patent No.: US 6,553,252 B2
(45) Date of Patent: Apr. 22, 2003

(54) METHOD AND SYSTEM FOR PREDICTING HUMAN COGNITIVE PERFORMANCE

(75) Inventors: Thomas J. Balkin, Ellicott City, MD (US); Gregory L. Belenky, Kensington, MD (US); Stanley W. Hall, Silver Spring, MD (US); Gary H. Kamimori, Laurel, MD (US); Daniel P. Redmond, Silver Spring, MD (US); Helen C. Sing, Takoma Park, MD (US); Maria L. Thomas, Columbia, MD (US); David R. Thorne, Washington, DC (US); Nancy Jo Wesensten, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 54 days.

(21) Appl. No.: 09/848,352

(22) Filed: May 4, 2001

(65) Prior Publication Data

US 2001/0021800 A1 Sep. 13, 2001

Related U.S. Application Data

(62) Division of application No. 09/389,350, filed on Sep. 3, 1999, now Pat. No. 6,419,629.

(60) Provisional application No. 60/122,407, filed on Mar. 2, 1999, and provisional application No. 60/106,419, filed on Oct. 30, 1998.

(51) Int. Cl.[7] .................................................. A61B 5/00
(52) U.S. Cl. ....................... 600/544; 600/545; 600/300; 128/903; 128/920
(58) Field of Search .................... 600/300–301, 600/544–545; 128/903, 904, 920, 923, 898; 434/236–238, 219–220, 118; 702/19

(56) References Cited

U.S. PATENT DOCUMENTS

| | | |
|---|---|---|
| 4,770,636 A | 9/1988 | Buschke |
| 4,893,291 A | 1/1990 | Bick et al. |
| 5,006,985 A | 4/1991 | Ehret et al. |
| 5,197,489 A | 3/1993 | Colan |
| 5,230,629 A | 7/1993 | Buschke |
| 5,259,390 A | 11/1993 | Maclean |
| 5,304,212 A | 4/1994 | Czeisler et al. |
| 5,348,370 A | 9/1994 | Fukuoka |
| 5,433,223 A | 7/1995 | Moore-Ede et al. |

(List continued on next page.)

OTHER PUBLICATIONS

Akerstedt et al., "Subjective and Objective Sleepiness in the Active Individual," International Journal of Neuroscience, 1990, vol. 52, pp. 29–37.

Angus et al., "Effects of Sleep Loss on Sustained Cognitive Performance During a Command and Control Stimulation," Behavior Research Methods, Instruments, & Computers, 1985, vol. 17, No. 1, pp. 55–67.

Beersma, Domien G. M., "Models of Human Sleep Regulation," Sleep Medicine ReviewS, 1998, vol. 2, No. 1, pp. 31–43.

Cole et al., "Automatic Sleep/Wake Identification from Wrist Activity," Sleep, 1992 vol. 15, No. 5, pp. 461–469.

(List continued on next page.)

Primary Examiner—Max F. Hindenburg
Assistant Examiner—Michael Astorino
(74) Attorney, Agent, or Firm—Elizabeth Arwine

(57) ABSTRACT

An apparatus and method for predicting cognitive performance of an individual based on factors including sleep history and the time of day. The method facilitates the creation of predicted cognitive performance curves that allow an individual to set his/her sleep times to produce higher levels of cognitive performance. The method also facilitates the reconstruction of past cognitive performance levels based on sleep history.

51 Claims, 19 Drawing Sheets

U.S. PATENT DOCUMENTS

| | | | |
|---|---|---|---|
| 5,566,067 A | 10/1996 | Hobson et al. | |
| 5,568,127 A | 10/1996 | Bang | |
| 5,570,698 A | 11/1996 | Liang et al. | |
| 5,573,013 A | 11/1996 | Conlan | |
| 5,585,785 A | 12/1996 | Gwin et al. | |
| 5,595,488 A | 1/1997 | Gozlan et al. | |
| 5,647,633 A | 7/1997 | Fukuoka | |
| 5,682,144 A | 10/1997 | Mannik | |
| 5,682,882 A | 11/1997 | Liberman | |
| 5,689,241 A | 11/1997 | Clarke Sr. et al. | |
| 5,691,693 A | 11/1997 | Kithil | |
| 5,720,294 A | 2/1998 | Skinner | |
| 5,762,072 A | 6/1998 | Conlan et al. | |
| 5,813,993 A | 9/1998 | Kaplan et al. | 600/544 |
| 5,911,581 A * | 6/1999 | Reynolds et al. | 434/236 |
| 5,995,868 A | 11/1999 | Dorfmeister et al. | 600/544 |
| 6,066,092 A * | 5/2000 | Cady et al. | 600/300 |
| 6,070,098 A | 5/2000 | Moore-Ede et al. | 600/544 |
| 6,113,538 A | 9/2000 | Bowles et al. | |
| 6,241,686 B1 * | 6/2001 | Balkin et al. | 600/544 |
| 6,287,262 B1 | 9/2001 | Amano et al. | |
| 6,419,629 B1 | 7/2002 | Balkin et al. | |
| 2002/0005784 A1 | 1/2002 | Balkin et al. | 340/573.1 |
| 2002/0017994 A1 | 2/2002 | Balkin et al. | |

OTHER PUBLICATIONS

Belenky, et al., "Sustaining Performance During Continuous Operations: The U.S. Army's Sleep Management System," Proceedings of the Army Science Conference, 1996, pp. 1–5.

Bonnet, M. H., "Sleep Restoration as a Function of Periodic Awakening, Movement, or Electroencephalographic Change," Sleep, 1987, vol. 10, No. 4, pp. 364–373.

Colburn et al, "An Ambulatory Activity Monitor with Solid State Memory," paper presented at the 13$^{th}$ Annual Rocky Mountain Bioengineering Symposium and 13$^{th}$ International ISA BioMedical Sciences Instrumentation Symposium (Instrument Society of America), May 3–5, 1976, pp. 117–122.

Dinges et al., "Cumulative Sleepiness, Mood Disturbance, and Psychomotor Vigilance Performance Decrements During a Week of Sleep Restricted to 4–5 Hours per Night," Sleep, 1997, vol. 20, No. 4, pp. 267–277.

Dinges et al., "Principles and Guidelines for Duty and Rest Scheduling in Commercial Aviation," NASA Technical Memorandum 110404, May 1996, pp. 1–10.

Dijk et al., "Paradoxical Timing of the Circadian Rhythm of Sleep Propensity Serves to Consolidate Sleep and Wakefulness in Humans," Neuroscience Letters, vol. 166, No. 1, pp. 63–68.

Edgar et al., "Effect of SCN Lesions on Sleep in Squirrel Monkeys: Evidence for Opponent Processes in Sleep–Wake Regulation," Journal of Neuroscience, Mar. 1993, vol. 13, No. 3, pp. 1065–1079.

Fischler, Benjamin, "Review of Clinical and Psychobiological Dimensions of the Chronic Syndrome: Differentiation from Depression and Contribution of Sleep Dysfunctions," Sleep Medicine Reviews, 1999, vol. 3, No. 2, pp. 131–146.

Fletcher et al., "A Predicative Model of Work–related Fatigue Based on Hours of Work," Journal of Occupational Health and Safety, 1997, vol. 13, No. 5, pp. 471–485.

Hendy et al., "Combining Time and Intensity Effects in Assessing Operator Information–Processing Load," Human Factors, 1997, vol. 39, No. 1, pp. 30–47.

Hockey, G. Robert J., "Compensatory Control in the Regulation of Human Performance under Stress and High Workload: A Cognitive–energetical Framework," Biological Psychology, 1997, vol. 45, pp. 73–93.

Hoddes et al., "Quantification of Sleepiness: A New Approach," Psychophysiology, Jul. 1973, vol. 10, No. 4, pp. 431–436.

Johns et al., "Daytime Sleepiness, Snoring, and Obstructive Sleep Apnea: The Epworth Sleepiness Scale," Chest, Jan. 1993, vol. 103, No. 1, pp. 30–36.

Johns, Murray, "Rethinking the Assessment of Sleepiness," Sleep Medicine Reviews, 1998, vol. 2, No. 1, pp. 3–15.

Kripke et al., "Wrist Actigraphic Measures of Sleep and Rhythms," Electroencephalography and Clinical Neurophysiology, 1978, vol. 44, pp. 674–676.

Lubin et al., "Effects of Exercise, Bedrest and Napping on Performance Decrement During 40 Hours," Psychophysiology, vol. 13, No. 4, pp. 334–339.

Mitler et al., "Methods of Testing for Sleepiness," Behavioral Medicine, 1996, vol. 21, pp. 171–183.

Monk et al., "A Parallelism between Human Body Temperature and Performance Independent of the Endogenous Circadian Pacemaker," Journal of Biological Rhythms, Apr. 1998, vol. 13, No. 2, pp. 113–122.

Newhouse et al., "Stimulant Drug Effects on Performance and Behavior After Prolonged Sleep Deprivation: A Comparison of Amphetamine, Nicotine, and Deprenyl," Military Psychology, 1992, vol. 4, pp. 207–233.

Newhouse et al., "The Effects of d–Amphetamine on Arousal, Cognition, and Mood After Prolonged Total Sleep Deprivation," Neuropsychopharmacology, 1989, vol. 2, No. 2, pp. 153–164.

Penetar et al., "Amphetamine Effects on Recovery Sleep Following Total Sleep Deprivation," Human Psychopharmacology, 1991, vol. 6, pp. 319–323.

Redmond et al, "Observations on the Design and Specifications of a Wrist–Worn Human Activity Monitoring System," Behavior Research Methods, Instruments, & Computers, 1985, vol. 17, Issue 6, pp. 659–669.

Rosekind, M.R. et al., "Alertness Management in Long–Haul Flight Operations," Proceedings of the 39$^{th}$ Annual Corporate Aviation Safety Seminar, 1994, pp. 167–178 (printed from the NASA website).

Shi, Yuhui et al., "Using Artificial Neural Network for Sleep/Wake Discrimination from Wrist Activity: Preliminary Results," Proceedings of the 20$^{th}$ Annual International Conference of the IEEE Engineering in Medicine and Biology Society, 1998, vol. 20, No. 3, pp. 1113–1115.

Thomas et al., "Regional Cerebral Metabolic Effects of Prolonged Sleep Deprivation" NeuroImage, 1998, vol. 7, No. 3, p. S130.

Thorne et al., "Plumbing Human Peformance Limits During 72 Hours of High Task Load," Proceedings of the 24$^{th}$ DRG Seminar on the Human as a Limiting Element in Military Systems, Defense and Civil Institute of Environmental Medicine, pp. 17–40 (1983).

Van Someren, Eus J. W., "Actigraph Monitoring of Movement and Rest–Activity Rhythms in Aging, Alzheimer's Disease, and Parkinson's Disease," IEEE Transactions on Rehabilitation Engineering, Dec. 1997, vol. 5, No. 4, pp. 394–398.

Advertiser flyer for "The Actiwatch–Score," Cambridge Neurotechnology.

Advertiser flyer for "The Actiwatch Software," Cambridge Neurotechnology.

Advertiser flyer for "The Actiwatch and Actiwatch Plus," Cambridge Neurotecnology.

Cambridge Neurotechnology, printouts from company website at http://www.camntech.co.uk/main.html, Sep. 18, 1998.

* cited by examiner

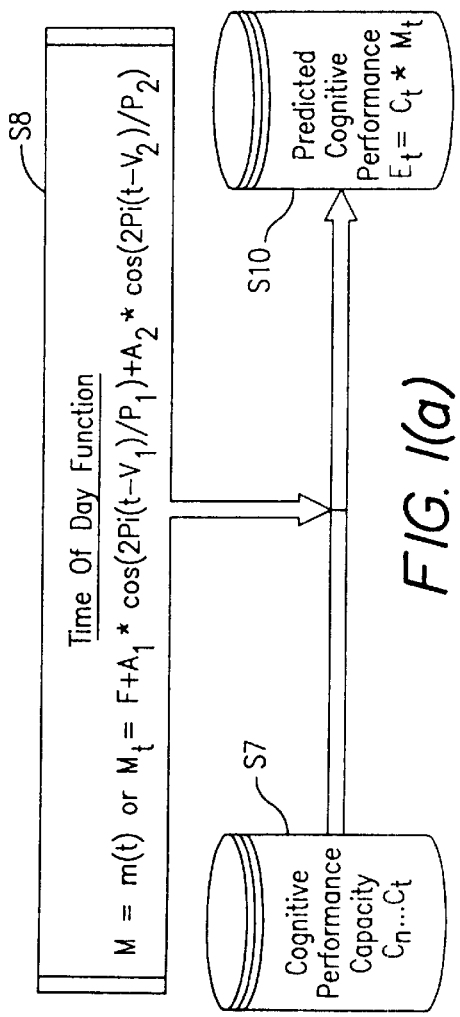
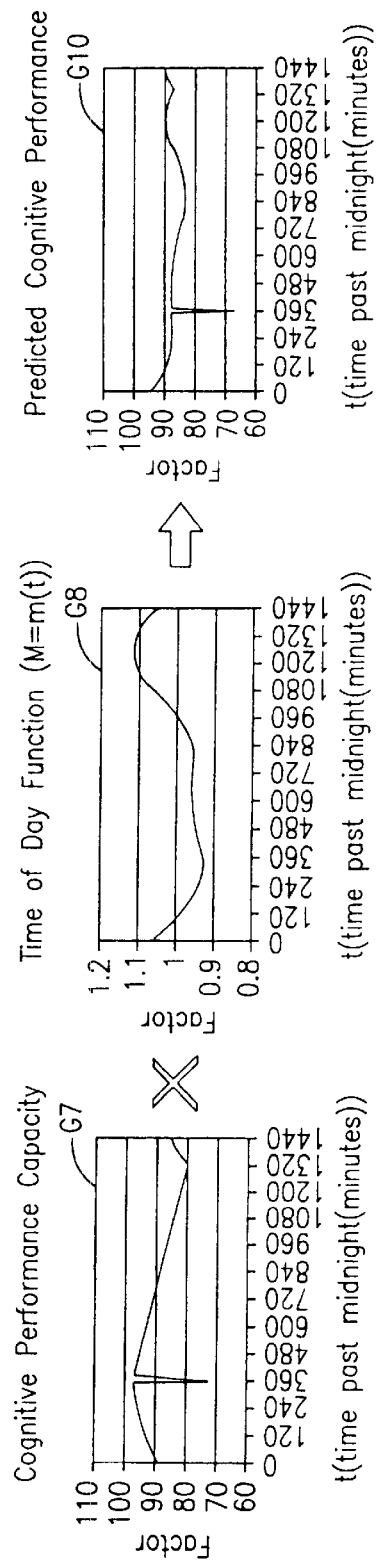
FIG. 1(a)
FIG. 1(b)

US 6,553,252 B2

METHOD AND SYSTEM FOR PREDICTING HUMAN COGNITIVE PERFORMANCE

This application is a divisional of U.S. patent application Ser. No. 09/389,350, filed on Sep. 3, 1999 now U.S. Pat. No. 6,419,629, which claims benefit of both U.S. provisional Application Serial No. 60/106,419, filed on Oct. 30, 1998 and U.S. provisional Application Serial No. 60/122,407, filed on Mar. 2, 1999. These patent applications are hereby incorporated by reference.

FIELD OF THE INVENTION

This invention relates to a method for predicting cognitive performance of an individual based on that individual's prior sleep/wake history and the time of day.

BACKGROUND OF THE INVENTION

Maintenance of productivity in any workplace setting depends upon effective cognitive performance at all levels from command/control or management down to the individual soldier or worker. Effective cognitive performance in turn depends upon complex mental operations. Many factors have been shown to affect cognitive performance (e.g., drugs or age). However, of the numerous factors causing day to day variations in cognitive performance, two have been shown to have the greatest impact. These two factors are an individual's prior sleep/wake history and the time of day.

Adequate sleep sustains cognitive performance. With less than adequate sleep, cognitive performance degrades over time. An article by Thorne et al. entitled "Plumbing Human Performance Limits During 72 hours of High Task Load" in Proceedings of the 24th DRG Seminar on the Human as a Limiting Element in Military Systems, Defense and Civil Institute of Environmental Medicine, pp. 17–40 (1983), an article by Newhouse et al. entitled "The Effects of d-Amphetamine on Arousal, Cognition, and Mood After Prolonged Total Sleep Deprivation" published in *Neuropsychopharmacology*, vol. 2, pp. 153–164 (1989), and another article by Newhouse et al. entitled "Stimulant Drug Effects on Performance and Behavior After Prolonged Sleep Deprivation: A Comparison of Amphetamine, Nicotine, and Deprenyl" published in *Military Psychology*, vol. 4, pp. 207–233 (1992) all describe studies of normal volunteers in which it is revealed that robust, cumulative decrements in cognitive performance occur during continuous total sleep deprivation as measured by computer-based testing and complex operational simulation. In the Dinges et al. article entitled "Cumulative Sleepiness, Mood Disturbance, and Psychomotor Vigilance Performance Decrements During a Week of Sleep Restricted to 4–5 Hours Per Night" published in *Sleep*, vol. 20, pp. 267–277 (1997) it is revealed that on fixed, restricted daily sleep amounts, cumulative reduced sleep also leads to a cognitive performance decline. Thus, in operational settings, both civilian and military, sleep deprivation reduces productivity (output of useful work per unit of time) on cognitive tasks.

Thus, using computer-based cognitive performance tests, it has been shown that total sleep deprivation degrades human cognitive performance by approximately 25% for each successive period of 24 hours awake. However, it also has been shown that even small amounts of sleep reduce the rate of sleep loss-induced cognitive performance degradation: Belenky et al. in their article entitled "Sustaining Performance During Continuous Operations: The U.S. Army's Sleep Management System," published in 20th *Army Science Conference Proceedings*, vol. 2, pp. 657–661 (1996), disclose that a single 30-minute nap every 24 hours reduces the rate of cognitive performance degradation to 17% per day over 85 hours of sleep deprivation. This suggests that recuperation of cognitive performance during sleep accrues most rapidly early in the sleep period. No other factor besides the amount of sleep contributes so substantially and consistently to the normal, daily variations in cognitive performance.

In addition to sleep/wake history, an individual's cognitive performance at a given point in time is determined by the time of day. In the early 1950s, Franz Halberg and associates observed a 24-hour periodicity in a host of human physiologic (including body temperature and activity), hematologic, and hormonal functions, and coined the term 'circadian' (Latin for 'about a day') to describe this cyclic rhythm. Halberg showed that most noise in experimental data came from comparisons of data sampled at different times of day.

When humans follow a nocturnal sleep/diurnal wake schedule (for example, an 8-hour sleep/16-hour wake cycle, with nightly sleep commencing at approximately midnight), body temperature reaches a minimum (trough) usually between 2:00 AM and 6:00 AM. Body temperature then begins rising to a maximum (peak) usually between 8:00 PM and 10:00 PM. Likewise, systematic studies of daily human cognitive performance rhythms show that speed of responding slowly improves across the day to reach a maximum in the evening (usually between 8:00 PM and 10:00 PM) then dropping more rapidly to a minimum occurring in the early morning hours (usually between 2:00 AM and 6:00 AM). Similar but somewhat less consistent rhythms have been shown from testing based on various cognitive performance tasks. Thus, superimposed on the effect of total sleep deprivation on cognitive performance noted above was an approximately ±10% percent variation in cognitive performance over each 24-hour period.

Various measures have been shown to correlate, to some extent, with cognitive performance. These include objective and subjective measures of sleepiness (or its converse, alertness). Some individuals familiar with the art use "sleepiness" to indicate the opposite of "alertness" (as is the case in the present document). "Drowsiness" often is used interchangeably with "sleepiness" although some familiar with the art would argue that "sleepiness" pertains specifically to the physiological need for sleep whereas "drowsiness" refers more to the propensity or ability to fall asleep (independent of physiological sleep need) or the subjective feeling of lack of alertness. The term "fatigue" has been used as a synonym for "sleepiness" by the lay population, but those familiar with the art do not consider "fatigue" to be interchangeable with "sleepiness"—rather, "fatigue" is a broad term that encompasses more than just the effects of sleep loss per se on performance. Likewise, "cognitive performance" has been defined as performance on a wide variety of tasks, the most commonly used being vigilance tasks (tasks requiring sustained attention). From vigilance and other tasks, some researchers use accuracy as their measure of cognitive performance, while others use reaction time (or its inverse, speed). Still others use a measure that is calculated as speed multiplied by accuracy, that is the amount of useful work performed per unit of time (also known as throughput). Those familiar with the art generally agree that vigilance tasks are appropriate measures of cognitive performance under conditions of sleep deprivation, and that either reaction time (speed) or some measure that takes reaction time into account (e.g., throughput) is a valid and reliable way of measuring cognitive performance.

The Multiple Sleep Latency Test (MSLT) is a widely accepted objective measure of sleepiness/alertness. In the MSLT, individuals try to fall asleep while lying in a darkened, quiet bedroom. Various physiological measures used to determine sleep or wakefulness are recorded (eye movements, brain activity, muscle tone), and time taken to reach the first 30 seconds of stage 1 (light) sleep is determined. Shorter latencies to stage 1 are considered to indicate greater sleepiness (lower alertness). Sleep latencies under 5 minutes are considered to be pathological (i.e., indicative of a sleep disorder or sleep deprivation). During both total and partial sleep deprivation, latency to sleep on the MSLT (alertness) and performance decline (i.e., sleepiness as measured by MSLT increases). However, although there is a correlation between MSLT-determined sleepiness/alertness and cognitive performance (greater sleepiness as indexed by MSLT corresponding to poorer cognitive performance), this correlation has never been shown to be perfect and for the most part is not strong. As a result, the MSLT is a poor (i.e., unreliable) predictor of cognitive performance.

Subjective measures of sleepiness/alertness also have been shown to correlate (albeit weakly) with cognitive performance. Hoddes et al., in their article entitled "Quantification of Sleepiness: A New Approach" published in *Psychophysiology*, vol. 10, pp. 431–436 (1973) describe the Stanford Sleepiness Scale (SSS), a subjective questionnaire used widely to measure sleepiness/alertness. In the SSS, individuals rate their current level of sleepiness/alertness on a scale from 1 to 7, with 1 corresponding to the statement, "feeling active and vital; alert; wide awake" and 7 corresponding to the statement "almost in reverie; sleep onset soon; losing struggle to remain awake." Higher SSS scores indicate greater sleepiness. As with the MSLT, during both total and partial sleep deprivation, scores on the SSS increase. However, as with MSLT, the correspondence between SSS-determined sleepiness/alertness and cognitive performance decrements is weak and inconsistent. As a result, the SSS also is a poor predictor of cognitive performance. Some other examples of subjective measures of sleepiness/alertness include the Epworth Sleepiness Scale described by Johns in his article entitled "Daytime Sleepiness, Snoring, and Obstructive Sleep Apnea" published in *Chest*, vol. 103, pp. 30–36 (1993), and the Karolinska Sleepiness scale described by Akerstedt and Gillberg in their article entitled "Subjective and Objective Sleepiness in the Active Individual" published in *International Journal of Neuroscience*, vol. 52, pp. 29–37 (1990). The correspondence between these subjective measures and cognitive performance also is weak and inconsistent.

In addition, factors modifying cognitive performance may not correspondingly affect objective or subjective measures of sleepiness/alertness, and vice versa. For example, the Penetar et al. article entitled "Amphetamine Effects on Recovery Sleep Following Total Sleep Deprivation" published in *Human Psychopharmacology*, vol. 6, pp. 319–323 (1991), disclose that during sleep deprivation, the stimulant drug d-amphetamine improved cognitive performance but not sleepiness/alertness (as measured by the MSLT). In a similar study, caffeine given as a sleep deprivation countermeasure maintained elevated cognitive performance for over 12 hours while the effects on subjective sleepiness, vigor and fatigue transiently improved but then decayed. Thorne et al. in their article entitled "Plumbing Human Performance Limits During 72 hours of High Task Load" in Proceedings of the 24$^{th}$ DRG Seminar on the Human as a Limiting Element in Military Systems, Defense and Civil Institute of Environmental Medicine, pp. 17–40 (1983), describe how cognitive performance continues to decline over 72 hours of sleep deprivation whereas subjective sleepiness/alertness declined over the first 24 hours but subsequently leveled off. The findings that cognitive performance and measures of sleepiness/alertness are not always affected in the same way indicate that they are not interchangeable. That is, measures of sleepiness/alertness cannot be used to predict cognitive performance, and vice versa.

Methods and apparatuses related to alertness detection fall into five basic categories: a method/apparatus for unobtrusively monitoring current alertness level; a method/apparatus for unobtrusively monitoring current alertness level and providing a warning/alarm to the user of decreased alertness and/or to increase user's alertness level; a method/apparatus for monitoring current alertness level based on the user's responses to some secondary task possibly with an alarm device to warn the user of decreased alertness and/or to increase user's alertness level; methods to increase alertness; and a method/apparatus for predicting past, current, or future alertness.

These methods and apparatuses that unobtrusively monitor the current alertness level are based on an "embedded measures" approach. That is, such methods infer alertness/drowsiness from the current level of some factor (e.g., eye position or closure) assumed to correlate with alertness/drowsiness. Some recently issued patents of this type include U.S. Pat. No. 5,689,241 to J. Clarke, Sr., et al. disclosing an apparatus to detect eye closure and ambient temperature around the nose and mouth; U.S. Pat. No. 5,682,144 to K. Mannik disclosing an apparatus to detect eye closure; and U.S. Pat. No. 5,570,698 to C. Liang et al. disclosing an apparatus to monitor eye localization and motion to detect sleepiness. An obvious disadvantage of these types of methods and apparatuses is that the measures are likely detecting sleep onset itself rather than small decreases in alertness.

In some patents, methods for embedded monitoring of alertness/drowsiness are combined with additional methods for signaling the user of decreased alertness and/or increasing alertness. Recently issued patents of this type include U.S. Pat. No. 5,691,693 to P. Kithil describing a device that senses a vehicle operator's head position and motion to compare current data to profiles of "normal" head motion and "impaired" head motion. Warning devices are activated when head motion deviates from the "normal" in some predetermined way. U.S. Pat. No. 5,585,785 to R. Gwin et al. describes an apparatus and a method for measuring total handgrip pressure on a steering wheel such that an alarm is sounded when the grip pressure falls below a predetermined "lower limit" indicating drowsiness. U.S. Pat. No. 5,568,127 to H. Bang describes a device for detecting drowsiness as indicated by the user's chin contacting an alarm device, which then produces a tactile and auditory warning. U.S. Pat. No. 5,566,067 to J. Hobson et al. describes a method and an apparatus to detect eyelid movements. A change in detected eyelid movements from a predetermined threshold causes an output signal/alarm (preferably auditory). As with the first category of methods and apparatuses, a disadvantage here is that the measures are likely detecting sleep onset itself rather than small decreases in alertness.

Other alertness/drowsiness monitoring devices have been developed based on a "primary/secondary task" approach. For example, U.S. Pat. No. 5,595,488 to E. Gozlan et al. describes an apparatus and a method for presenting auditory, visual, or tactile stimuli to an individual to which the individual must respond (secondary task) while performing the primary task of interest (e.g., driving). Responses on the secondary task are compared to baseline "alert" levels for responding. U.S. Pat. No. 5,259,390 to A. MacLean describes a device in which the user responds to a relatively innocuous vibrating stimulus. The speed to respond to the stimulus is used as a measure of the alertness level. A disadvantage here is that the apparatus requires responses to a secondary task to infer alertness, thereby altering and possibly interfering with the primary task.

Other methods exist solely for increasing alertness, depending upon the user to self-evaluate alertness level and activate the device when the user feels drowsy. An example of the latter is U.S. Pat. No. 5,647,633 and related patents to M. Fukuoka in which a method/apparatus is described for causing the user's seat to vibrate when the user detects drowsiness. Obvious disadvantages of such devices are that the user must be able to accurately self-assess his/her current level of alertness, and that the user must be able to correctly act upon this assessment.

Methods also exist to predict alertness level based on user inputs known empirically to modify alertness. U.S. Pat. No. 5,433,223 to M. Moore-Ede et al. describes a method for predicting the likely alertness level of an individual at a specific point in time (past, current or future) based upon a mathematical computation of a variety of factors (referred to as "real-world" factors) that bear some relationship to alterations in alertness. The individual's Baseline Alertness Curve (BAC) is first determined based on five inputs and represents the optimal alertness curve displayed in a stable environment. Next, the BAC is modified by alertness modifying stimuli to arrive at a Modified Baseline Alertness Curve. Thus, the method is a means for predicting an individual's alertness level, not cognitive performance.

Another method has been designed to predict "work-related fatigue" as a function of number of hours on duty. Fletcher and Dawson describe their method in an article entitled "A Predictive Model of Work-Related Fatigue Based on Hours of Work" published in *Journal of Occupational Health and Safety*, vol. 13, 471–485 (1997). In this model a simplifying assumption is made—it is assumed that length of on-duty time correlates positively with time awake. To implement the method, the user inputs a real or hypothetical on-duty/off-duty (work/rest) schedule. Output from the model is a score that indicates "work-related fatigue." Although this "work-related fatigue" score has been shown to correlate with some performance measures, it is not a direct measure of cognitive performance per se. It can be appreciated that the fatigue score will be less accurate under circumstances when the presumed relationship between on-duty time and time awake breaks down—for example when a person works a short shift but then spends time working on projects at home rather than sleeping or when a person works long shifts but conscientiously sleeps all the available time at home. Also, this method is obtrusive in that the user must input on-duty/off-duty information rather than such information being automatically extracted from an unobtrusive recording device. In addition, the model is limited to predictions of "fatigue" based on work hours. Overall, this model is limited to work-related situations in which shift length consistently correlates (inversely) with sleep length.

Given the importance of the amount of sleep and the time of day for determining cognitive performance (and hence estimating productivity or effectiveness), and given the ever-increasing requirements of most occupations on cognitive performance, it is desirable to design a reliable and accurate method of predicting cognitive performance. It can be appreciated that increasing the number of relevant inputs increases cognitive performance prediction accuracy. However, the relative benefits gained from such inputs must be weighed against the additional burdens/costs associated with their collection and input. For example, although certain fragrances have been shown to have alertness-enhancing properties, these effects are inconsistent and negligible compared to the robust effects of the individual's sleep/wake history and the time of day. More important, the effect of fragrances on cognitive performance is unknown. Requiring an individual to keep a log of exposure to fragrances would be time consuming to the individual and only result in negligible gains in cognitive performance prediction accuracy. In addition, while the effects of the sleep/wake history and the time of day on cognitive performance are well known, the effects of other putative alertness-altering factors (e.g., job stress and workload), how to measure them (their operational definition), and their direction of action (cognitive performance enhancing or degrading) are virtually unknown.

An important and critical distinction between the present invention and the prior art is that the present invention is a model to predict performance on tasks with a cognitive component. In contrast, previous models involving sleep and/or circadian rhythms (approximately 24-hour) focused on the prediction of "alertness" or "sleepiness." The latter are concepts that specifically relate to the propensity to initiate sleep, not the ability to perform a cognitive task.

Although sleepiness (or its converse, alertness) could be viewed as an intervening variable that can mediate cognitive performance, the scientific literature clearly shows that cognitive performance and alertness are conceptually distinct, as reviewed by Johns in the article entitled, "Rethinking the Assessment of Sleepiness" published in *Sleep Medicine Reviews*, vol. 2, pp. 3–15 (1998), and as reviewed by Mitler et al. in the article entitled, "Methods of Testing for Sleepiness" published in Behavioral Medicine, vol. 21, pp. 171–183 (1996). Thomas et al. in the article entitled "Regional Cerebral Metabolic Effects of Prolonged Sleep Deprivation" published in *NeuroImage*, vol. 7, p. S130 (1998) reveal that 1–3 days of sleep loss result in reductions in global brain activation of approximately 6%, as measured by regional cerebral glucose uptake. However, those regions (heteromodal association cortices) that mediate the highest order cognitive functions (including but not limited to attention, vigilance, situational awareness, planning, judgment, and decision making) are selectively deactivated by sleep loss to a much greater extent—up to 50%—after three days of sleep loss. Thus, decreases in neurobiological functioning during sleep restriction/deprivation are directly reflected in cognitive performance degradation. These findings are consistent with studies demonstrating that tasks requiring higher-order cognitive functions, especially those tasks requiring attention, planning, etc. (abilities mediated by heteromodal association areas) are especially sensitive to sleep loss. On the other hand, brain regions such as primary sensory regions, are deactivated to a lesser degree. Concomitantly, performance (e.g., vision, hearing, strength and endurance tasks) that is dependent on these regions is virtually unaffected by sleep loss.

Consequently, devices or inventions that predict "alertness" per se (e.g., Moore-Ede et al.) putatively quantify the brain's underlying propensity to initiate sleep at any given point in time. That is, devices or inventions that predict "alertness" (or its converse "sleepiness") predict the extent to which sleep onset is likely. The present invention differs from such approaches in that the nature of the task is accounted for—i.e., it is not the propensity to initiate sleep that is predicted. Rather, the present invention predicts the extent to which performance of a particular task will be impaired by virtue of its reliance upon brain areas most affected by sleep deprivation (heteromodal association areas of the brain). The most desirable method will produce a highly reliable and accurate cognitive performance estimate based on the sleep/wake history of an individual and the time of day.

SUMMARY OF THE INVENTION

A feature of the present invention is that it provides a numerical representation of predicted cognitive performance with an immediate ergonomic and economic advantage, i.e., an indication of productivity or effectiveness of an individual. Another feature of the present invention is that it does not require or use measurements/computations that are indirect, intermediate, inferential or hypothetical concomitants of cognitive performance. Examples of the latter are alertness, sleepiness, time to sleep onset, body temperature and/or other physiological measures that vary with time. A further feature of the invention is that it accounts for transient or adventitious variations in cognitive performance from any source as a result of how that source affects the sleep/wake history (e.g., age) and/or physiological time of day (e.g., shift work). In effect, such sources are not treated as having effects on cognitive performance independent of the sleep/wake history and/or the time of day, and as such do not require separate measurement, tabulation, and input into the method.

One objective of this invention is to provide an accurate method for predicting cognitive performance of an individual.

A further objective is to provide a method that facilitates prediction of the effects of possible future sleep/wake histories on cognitive performance (forward prediction).

Another objective is to provide a method that facilitates retrospective analysis of likely prior cognitive performance based on the individual's sleep/wake history and the time of day.

Another objective is to provide a method for coordination and optimization of available sleep/wake time in order to obtain net optimal predicted cognitive performance for an individual and/or a group of individuals.

It can be appreciated that an implicit advantage and novelty of the method is its parsimony. The method uses those factors possessing maximal predictive value (as demonstrated empirically) as continuously updated inputs. Thus, the model will be simple to implement. Other models predicting "alertness" require the user to track multiple input variables (e.g., caffeine, alcohol ingestion, light/dark exposure, diurnal type), rather than presenting these inputs as optional "attachments" to a standard, simplified model based on those factors accounting for maximum cognitive performance change. For example, in accordance with a segment of the present method, the effects of age on cognitive performance are accounted for implicitly via the empirically derived effects of age on sleep. That is, sleep quality degrades with age. The inherent degradation in sleep quality with aging would implicitly result in a prediction of degraded cognitive performance (since in the present method degraded sleep results in a prediction of degraded cognitive performance), even if an individual's age were unknown. Therefore, age need not constitute a separate (independent) input variable to a cognitive performance prediction model.

The invention also provides other significant advantages. For example, an advantage of this invention is the elimination of a need for empirical evaluation.

Another advantage of this invention is obtaining an accurate prediction of cognitive performance of an individual. The advantage may be achieved by a method incorporating two factors that have been empirically demonstrated to exert a significant effect on cognitive performance, namely, (1) the individual's sleep/wake history and (2) the time of day ("day" herein referring to a 24-hour period including both nighttime and daylight hours).

Another advantage achieved by this invention is an accurate prediction of current cognitive performance.

Another advantage achieved by this invention is that it is capable of providing a real time prediction of cognitive performance.

Yet another advantage achieved by this invention is a prediction of future expected cognitive performance throughout the day based on hypothetical future sleep/wake periods.

An additional advantage achieved by this invention is a retrospective analysis of cognitive performance at given times.

Another advantage of the invention is that a particular cognitive performance prediction is not based on normative data (i.e., does not require a "look-up table" for output), but rather is calculated directly based on each individual's sleep/wake information and the time of day.

Another advantage of the invention is that it can be used to optimize the individual's future sleep/wake schedule based on a fixed mission/work schedule. Previous methods and apparatuses are directed toward modifying the work schedule and/or mission to "fit the individual". In most situations, however, work schedules and/or missions are fixed. Thus, modifying the work schedule or mission to suit the individual is impractical or impossible. A more reasonable approach incorporated in the present method is to allow the individual to adjust his/her sleep/wake periods to meet work/mission demands. Thus, the current method presents a more practical alternative by providing a means to regulate work hours to a directly applicable metric (cognitive performance) instead of regulating work hours by time off duty or by using indirect measures of cognitive performance such as alertness.

A feature of this invention is the provision of a graphical representation that translates an individual's sleep/wake history and the time of day into an immediately useful, self-evident index. A prediction of cognitive performance, unlike a prediction of "alertness" or "sleepiness", requires no further interpretation.

The method for predicting human cognitive performance in accordance with the invention accomplishes the above objectives and achieves the above advantages. The method and resulting apparatus are easily adapted to a wide variety of situations and types of inputs.

In accordance with an aspect of the invention, an individual sleep/wake history is inputted into a processing device. The processing device classifies the individual pieces of sleep/wake history data as either sleep or wake. Based on the classification of data, the processing device selects and calculates a cognitive performance capacity corresponding to the present state of the individual, the cognitive performance capacity may be modified by a time of day value to adjust the cognitive performance capacity to a predicted cognitive performance. The predicted cognitive performance represents the ability of the individual to perform cognitive tasks. The predicted cognitive performance may be displayed for a real-time indication or as part of a curve, printed out with the information that could have been displayed, and/or stored for later retrieval and/or use. The calculation of the cognitive performance capacity is made based on functions which model the effect of the interrelationship of sleep and being awake on cognitive performance. The time of day function models the effect of an individual's circadian rhythms on cognitive performance.

In accordance with the underlying method of the invention, the method can be accomplished with a wide variety of apparatus. Examples of the possible apparatus embodiments include electronic hardware as either dedicated equipment or equipment internal to a computer, software embodied in computer readable material for use by computers, software resident in memory or a programmed chip for use in computers or dedicated equipment, or some combination of both hardware and software. The dedicated equipment may be part of a larger device that would complement the dedicated equipment's purpose.

Given the following enabling description of the drawings, the invention should become evident to a person of ordinary skill in the art.

DESCRIPTION OF THE DRAWINGS

FIG. 1(a) is a block diagram representation of the modulation in the preferred embodiment. FIG. 1(b) graphically shows the combination of output from the functions represented by FIG. 3(a) with time of day modulation to derive predicted cognitive performance.

DETAILED DESCRIPTION OF THE INVENTION

The present invention involves a method for predicting cognitive performance at a given time in the past, present, or future as a consequence of the amount of sleep and wakefulness up to that time and further as a function of the time of day. The method calculates a numerical estimate of cognitive performance for an individual as a continuous function of time. The calculations (described below) are based on empirically derived direct mathematical relationships among (1) the continuous decrement of cognitive performance during wakefulness; (2) restoration of cognitive performance during sleep; and (3) cyclic variation in cognitive performance during the course of the day.

Figure 2:
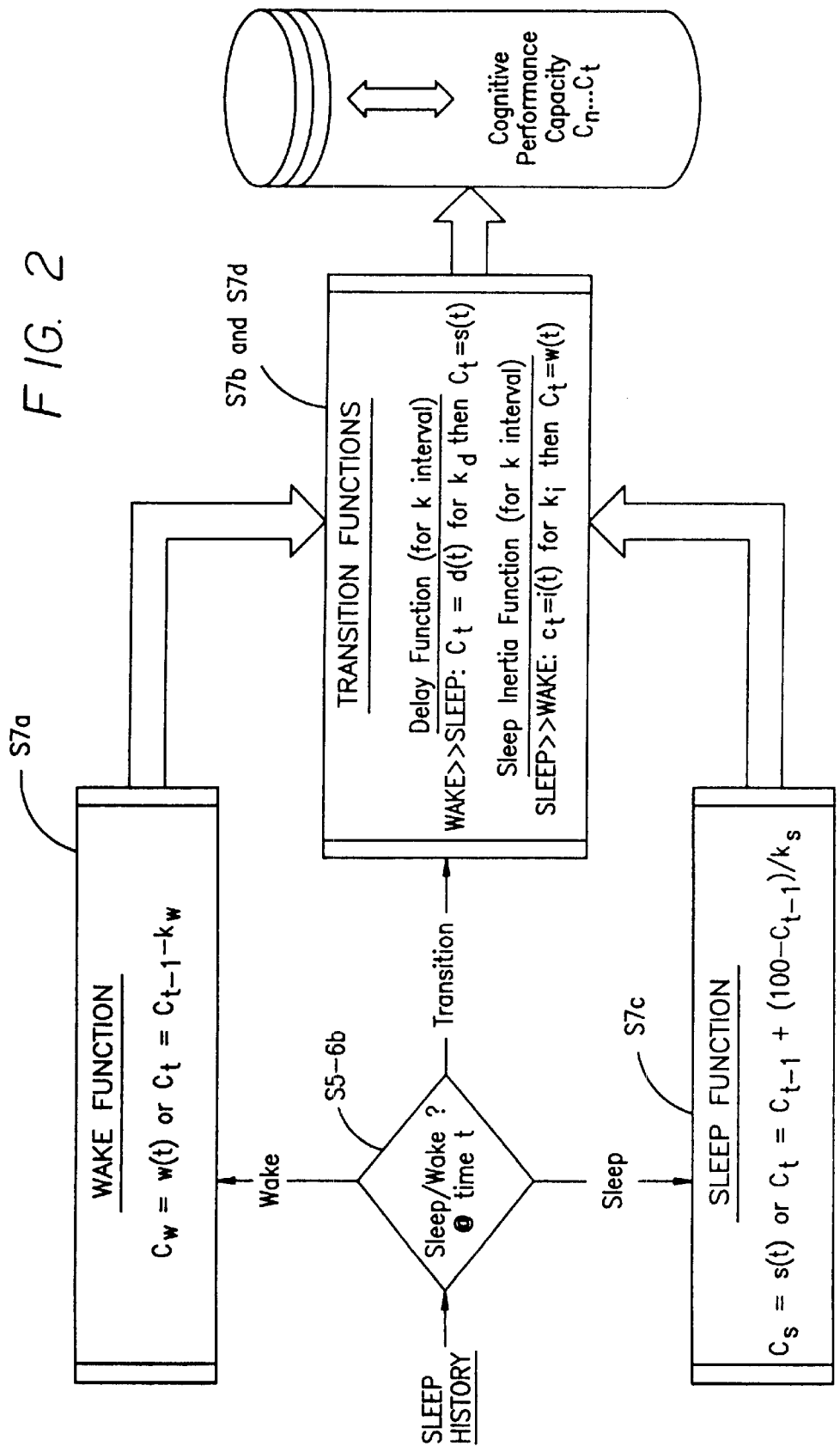
FIG. 2 is a block diagram representation of the wake, sleep, delay, and sleep inertia functions for calculating predicted cognitive performance capacity.

In accordance with the invention, a numeric value indicating predicted cognitive performance at a given moment in time is provided as shown in FIGS. 1(a)–4(b). As shown in FIGS. 1(a)–(b), predicted cognitive performance equals the output of a series of calculations obtained in three general steps, using functions empirically derived from direct measurements of cognitive performance under scientifically controlled conditions. The first step, as shown in FIG. 2, uses a set of functions to calculate an initial value referred to as the level of cognitive performance capacity as graphically depicted in FIGS. 3(a)–(c). Once the level of cognitive performance capacity is calculated, the second step calculates or uses a previously calculated time of day modulator M represented as G8 in FIG. 1(b) and S8 in FIG. 4(b). The third step involves the mathematical combination of the results from the first and second steps yielding predicted cognitive performance, shown as a block diagram in FIG. 1(a) and graphically represented in FIG. 1(b).

There are four functions relating to the sleep/wake history used to calculate the level of cognitive performance capacity as shown in FIGS. 2–4(b). The wake function w(t) quantifies empirically derived relationships between the time awake and degradation of cognitive performance. The sleep function s(t) quantifies empirically derived relationships between the time asleep and maintenance and/or recuperation of cognitive performance. In addition to these two primary functions that operate during the bulk of the time awake or asleep there are two other functions that operate briefly during the transition from one state to the other. They include the delay of recuperation function d(t) and the sleep inertia function i(t). The delay of recuperation function d(t) represents the relationship between the wake to sleep transition and the recuperation of cognitive performance. This function operates during the initial period of sleep following being awake, known as stage 1 sleep, as shown in FIG. 3(b). The sleep inertia function i(t) represents the relationship between the sleep to wake transition and cognitive performance. This function operates during the initial period of time being awake after being asleep as shown in FIG. 3(c).

The function representing the time of day M's effects on cognitive performance is used to calculate a modulating factor. The time of day function describes empirically derived relationships between the time of day (point in time within a 24-hour period) and the variation in cognitive performance over the course of the day as exemplified by G8 in FIG. 1(b).

A mathematical operation, shown in FIG. 1(b) as multiplication, is used to combine the results from the first and second steps into a single predicted cognitive performance curve E in the third step.

The inputted data S2 into the method includes a representation of an individual's sleep/wake history. The sleep/wake history is a time series or temporal record based on local clock time. Each successive period, interval or epoch identifies one of two mutually exclusive states, namely wake or sleep. Examples of this input include, but are not limited to: (1) self-estimated sleep/wake times, e.g., as noted by the individual into a sleep diary or sleep log; (2) observer-estimated sleep/wake times, e.g., as recorded by someone observing the individual; or (3) objectively monitored sleep/wake times, e.g., as scored from a polysomnogram, activity monitor, or estimated from pneumatic, acoustic, biochemical, electrophysiological or other sensors. Such a sleep/wake history is not necessarily "historical" in the sense of occurring in the past, but may for example be hypothetical, projected, idealized, or contemplated. The latter, in particular, are appropriate for the predictive uses of this method.

The gold standard for measuring sleep and wakefulness is polysomnography (PSG). PSG sleep scoring is based on the concurrent recording, or at least recording in such a way as allows the latter synchronization (typically with time-stamping or time-linking) of the data, of electroencephalogram (EEG), electrooculogram (EOG), and electromyogram (EMG). These signals are then visually inspected on an epoch-by-epoch basis (each epoch traditionally is 30 seconds in length for PSG) to determine an individual's stage of sleep or wakefulness. Polysomnographic sleep scoring distinguishes between wake, non-rapid eye movement sleep (NREM) and rapid eye movement sleep (REM), with NREM sleep being further distinguished into four stages (stages 1, 2, 3, and 4) on the basis of characteristic EEG markers. PSG is not a practical method for determining sleep and wakefulness in applied settings (e.g., while driving, working, or on the battlefield), because PSG requires that individuals be attached to sensors or electrodes that connect with a recording device, and currently the only accepted method for scoring PSG is by visual inspection of the recorded EEG, EOG, and EMG results.

Presently, if a computer is used for scoring PSG, then typically a human reviews the results for accuracy in the scoring, because computer scoring has not been approved by the American Sleep Disorders Association. Also, recently, researchers have been exploring whether spectrally analyzed PSG or similar data using Fast Fourier Transforms might provide a better measurement of sleep in humans than PSG scoring.

A preferred method of determining sleep from wakefulness would be a device that is portable, unobtrusive, reliable, and whose recordings can be scored automatically. One such method is monitoring of movement activity, or actigraphy. The movement activity device is typically worn on the non-preferred wrist, but may be placed elsewhere on an individual (e.g., the ankle). When worn on the non-preferred wrist, these devices have been shown to accurately quantify sleep and wakefulness as compared to the standard provided by PSG (reliabilities as high as 90%).

The most widely used method of scoring actigraphy data is an algorithm developed by Cole and associates and described in their article entitled "Automatic Sleep/Wake Identification from Wrist Actigraphy" published in *Sleep*, vol. 15, pp. 461–469 (1992). Successful actigraphy sleep-scoring algorithms such as the Cole et al. algorithm (also known as the Cole-Kripke algorithm) are for use with conventional (number-of-zero-crossings) actigraphs, and some algorithms account for the number of counts above a certain threshold. These algorithms are limited to making simple sleep vs. wake distinctions, and cannot distinguish sleep stage changes (e.g., Stage 1 to Stage 2, or Stage 2 to REM) within sleep itself. Consequently, such algorithms cannot discriminate recuperative sleep (stages 2, 3, 4, and REM) from non-recuperative sleep (stage 1).

More recently, digital signal processing (DSP) actigraphs have begun to be developed. Because the DSP actigraph will provide much more information than just the conventional number of zero crossings or counts above threshold (this and other information provided by a conventional actigraph will, however, be retained), it shows promise for distinguishing between different sleep stages. Thus, sleep scoring systems for DSP will not only replace, but will also make irrelevant, the Cole-Kripke algorithm. A sleep scoring system for the DSP will be developed as the DSP database of empirical data from use of DSP actigraphs increases.

Other algorithms and methodologies for automated actigraphy scoring have been developed by, for example, Jean-Louis et al., 1996; Sadeh et al., 1989; and Zisapel et al., 1995. Each of these scoring systems shows considerable promise, especially for scoring the actigraphically recorded sleep/wake states of individuals with sleep disorders or other medical disorders. Available scoring systems mainly differ along technical aspects, for example, the extent to which activity counts in previous and subsequent epochs influence the scoring of the current epoch; and variation among mathematical principles underlying each scoring system. As one of ordinary skill in the art will realize, any actigraph scoring system is capable of providing the sleep/wake data input for the method of this invention.

The sleep/wake history will preferably take the form of a data series. The sleep/wake history may include past, present, and/or future (predicted) sleep/wake patterns of an individual. The sleep/wake history is a representation of a state of an individual as either being asleep or awake and is divided into epochs. The epochs are the same length, but that length could be of any time period as dictated by restraints of the method and apparatus used to collect data and/or the desired precision of the sleep/wake pattern. The PSG or similar scoring can be converted into a sleep/wake history for an individual.

It can be appreciated that the accuracy of the cognitive performance prediction is directly related to the accuracy of the sleep/wake history input and the sleep scoring system used to interpret the sleep/wake states of an individual. One possible source of inaccuracy may arise from the temporal resolution of the input epoch or interval. That is, the shorter the input epoch, the higher the temporal resolution and consequent moment-to-moment accuracy of the sleep/wake input. For example with actigraphy, past experience indicates that the most effective length of an epoch is one minute. Another source of inaccuracy may arise from ambiguity in the sleep/wake discrimination itself. In the event that the history input is ambiguous (i.e., the sleep or wake state is uncertain), the calculation of predicted cognitive performance can be performed twice concurrently, once for each possible state (sleep or wake), resulting in a dual output representing the possible range of expected cognitive performance. One of ordinary skill in the art will appreciate that the dual output can be further divided if there is more than one ambiguity in the sleep/wake history. Such treatment in executing the functions expressed below is included as a component of this method and any implementing apparatus.

The method of this invention is not limited with regard to time or technique: on-line/real-time vs. off-line/post-hoc; or incremental, iterative vs. discrete solutions to continuous forms of those equations.

A preferred embodiment of the method encompasses a mathematical model that expresses predicted cognitive performance capacity E at time t as a modulation of the current cognitive performance capacity C by a time of day function M. It can be written as a general description in its simplest form as:

$$E = C \nabla M \quad \text{Equation 1}$$

where $\nabla$ represents a mathematical operator. Any mathematical operator may be used to combine cognitive performance capacity C and day of time function M. The form and nature of time of day function M dictates the exact operator that is most desirable. Most preferably, Equation 1a below would be used to combine cognitive performance capacity C and day of time function M.

$$E = C * M \quad \text{Equation 1a}$$

In the alternative, Equation 1b below could also be used to combine cognitive performance capacity C and day of time function M.

$$E = C + M \quad \text{Equation 1b}$$

Cognitive performance capacity C represents a function of sleep/wake history, that is $$C = w(t) + s(t) + d(t) + i(t) \quad \text{Equation 2}$$

where $w(t)$, $s(t)$, $d(t)$, and $i(t)$ are the instantaneous values of the wake, sleep, delay, and sleep inertia functions at time t. Time of day function M represents a function of the time of day, such that $$M = m(t) \quad \text{Equation 3}$$

where $m(t)$ is the instantaneous value of the time of day function at time t.

Figure 4A:
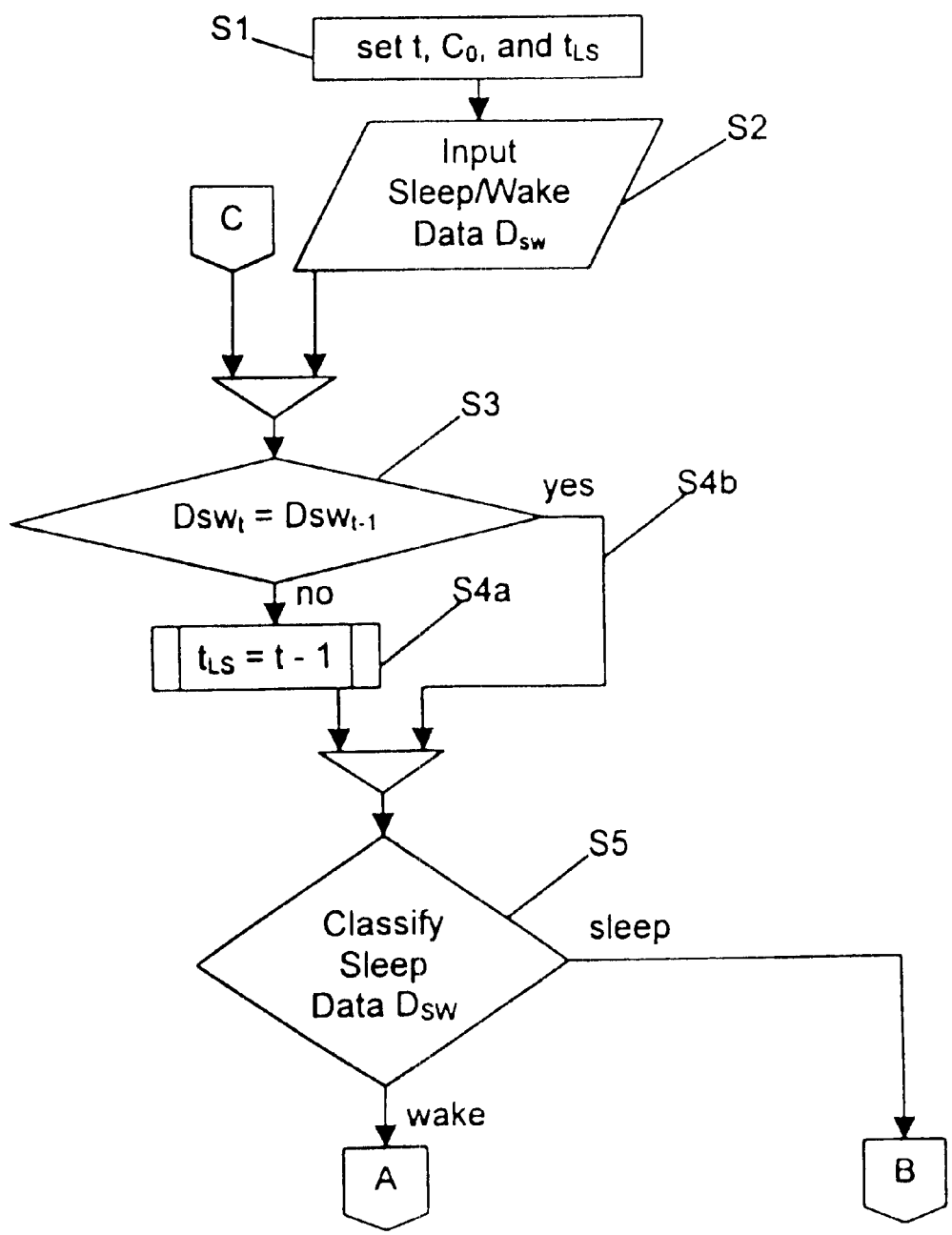
FIGS. 4(a)–(b) depict a detailed flowchart showing the steps of the method of the invention.

In keeping with the invention, a three-step process may be performed after either an initial setting of the starting time t, the starting cognitive performance capacity C, and the time of the last transition $t_{LS}$ when appropriate in S1 of FIG. 4(a) where these data can be entered in any order. In the first step, the level of cognitive performance capacity C at time t may be calculated based on an individual's sleep/wake history using functions $w(t)$, $s(t)$, $d(t)$, and $i(t)$ as represented by S3–S7e in FIGS. 4(a)–(b). In the second step, time of day modulator M may be calculated using the time of day function as represented by S8 in FIG. 4(b). According to an aspect of the invention, the second step can be performed once to provide a series of data points in time sequential order for multiple executions of the first step. In the third step, predicted cognitive performance E may be derived from the combination of cognitive performance capacity C and time of day modulator M resulting in cognitive performance capacity C being modulated by time of day modulator M as illustrated by S9 in FIG. 4.

First Step: Calculation of Cognitive Performance Capacity C

FIG. 2 is a schematic flow diagram representing the use of the functions described below. Examples of the calculations discussed are graphically illustrated in FIGS. 3(a)–(c). FIGS. 4(a)–(b) are a detailed flowchart of the steps in the method. As a preferred embodiment of the model, cognitive performance capacity C is herein assigned values having a total range of zero to 100 and thus represent percentages. The ranges in this application are intended to encompass the end points of the stated numerical range. However, cognitive performance capacity C may be scaled to other values or units for specific applications.

In the preferred embodiment, only one of the four functions $w(t)$, $s(t)$, $d(t)$, and $i(t)$ operates at any given interval of time, and the others are equivalent to zero in Equation 2 as represented by S7a through S7d. Functions $w(t)$ and $s(t)$ describe the non-transition states, while functions $d(t)$ and $i(t)$ describe the transition states. For instance in a non-transition state, when the individual is awake, function $s(t)$ is set to zero, and when the individual is asleep, function $w(t)$ is set to zero. Likewise, during specific intervals of transition from wake to sleep and vice versa, only one of the transition functions $d(t)$ or $i(t)$ operates, the other being set equal to zero. When there is a change between sleep and wake, or vice versa, a time counter $t_{LS}$ is reset to keep track of the time in the present state for determining decision rules for the transition functions $d(t)$ and $i(t)$ as shown in FIG. 4(b).

(1) Wake Function (w(t))

The wake function S7a represents the depletion of cognitive performance capacity with the passage of time awake. It is based on evidence that (1) near-100% cognitive performance is maintained from day to day when individuals obtain eight hours of sleep each night; and (2) cognitive performance appears to decline by approximately 25% for every 24 hours of wakefulness.

In S7a, the wake function $w(t)$ calculates the current value of cognitive performance capacity C resulting from the decay in cognitive performance capacity that occurs over an interval of time from t−1 to t, which in the preferred embodiment is the length of one epoch. As noted above, this calculation is performed independent of and prior to modulation of cognitive performance capacity C by the time of day function M in S9. A generalized form of the wake function is given by the equation:

$$C_W = w(t) \quad \text{Equation 4}$$

where wake function $w(t)$ may be any positive-valued function decreasing with t. More preferably, the wake function $w(t)$ is a linear function depleting performance at a constant rate, and, most preferably, the wake function $w(t)$ is expressed at time t as follows:

$$w(t) = C_{t-1} - k_w \quad \text{Equation 4a}$$

where the interval of wakefulness is from t−1 to t (in epochs) and the decay in performance per minute is $k_w$. Thus, if t−1 to t is not one minute, then $k_w$ is appropriately adjusted. The total range of $k_w$ is any positive real number, and preferably $k_w$ is a range of 0.003 to 0.03% per minute, and most preferably $k_w$ is equal to approximately 1% per hour or 0.017% per minute. The value $k_w$ is based on empirical data showing that cognitive performance declines by approximately 25% for every 24 hours of continuous wakefulness. Equation 4a is represented in FIGS. 2 and 4(b) at S7a. An example is illustrated as the wake function in FIG. 3(a), for an initial cognitive performance capacity of 100%, a decay rate of 0.017% per minute, over an interval of 16 hours (960 minutes).

(2) Sleep Function (s(t))

The sleep function S7c restores cognitive performance capacity with the passage of time asleep. The sleep function $s(t)$ is based on empirical evidence that the recuperative value of sleep on cognitive performance accumulates in a nonlinear manner. That is, the rate of cognitive performance capacity recuperation is higher initially during sleep and slows as the time asleep accumulates. Other data indicates that sleep beyond a certain point confers little or no additional benefit for cognitive performance and the rate of recuperation approaches zero. Thus, for example, two hours of sleep are not twice as recuperative as one hour of sleep. The sleep function increases cognitive performance capacity at a rate that depends on the current level of cognitive performance capacity—the lower the initial cognitive performance capacity, the more rapidly recuperation accumulates. For example, following a full day (16 hours) of wakefulness, during ensuing nighttime sleep recuperation accumulates rapidly early in the night. As cognitive performance capacity is restored across the sleep period, the rate of recuperation declines. Following sleep deprivation, initial cognitive performance capacity is even lower than it would be following a normal 16-hour day, and the rate of recuperation is even higher than at the beginning of recovery sleep. During chronic partial sleep deprivation, cognitive performance capacity may not be completely restored each night despite this more rapid initial recuperation rate.

The sleep function calculates the current value of cognitive performance capacity C resulting from the recovery of capacity that occurs while an individual is asleep over an interval of time T (from t−1 to t). As noted above, this calculation is performed independent of, and prior to, modulation of C by the time of day function M. A generalized form of the sleep function is given by the equation:

$$C_S = s(t) \qquad \text{Equation 5}$$

where sleep function s(t) may be any positive-valued function increasing with t, and more preferably the sleep function s(t) is an exponential function. This is based on empirical data showing that cognitive performance restoration during sleep is nonlinear, with the rate of recuperation highest initially and gradually slowing as sleep continues. Thus, the most preferred sleep function is an exponential function, which in its discrete form is stated as:

$$C_t = C_{t-1} + (100 - C_{t-1})/k_s \qquad \text{Equation 5a}$$

where the interval of sleep is from t−1 to t (in minutes), the maximum cognitive performance capacity value is 100%, $C_{t-1}$ is cognitive performance capacity in the period preceding time t, and $k_s$ is the recuperation "time constant". In other words, $k_s$ is the time required to fully restore cognitive performance capacity C if it was restored at a constant rate equal to the initial slope of the curve. The recuperation time constant $k_s$ is derived empirically from partial sleep deprivation data and is selected based on the length of the epoch. In accordance with the preferred embodiment, $k_s$ is equal to any positive real number. For example, $k_s$ may be in the range of 100 to 1000, and, more particularly may be approximately 300 with an epoch length of one minute. However, the optimum values for $k_s$ will depend at least in part on the length of the epoch. Equation 5a is represented in FIGS. 2 and 4(b) as S7c. A graphical example is illustrated as the sleep function in FIG. 3(a), using an initial cognitive performance capacity level of 100, and using a time period of one minute and $k_s$=300, the effect of eight hours of sleep following 16 hours of wakefulness.

(3) Delay Function d(t) for Wake to Sleep Transitions

The delay of recuperation function d(t) defines the duration of an interval after sleep onset during which recuperation of cognitive performance capacity from the sleep function is delayed. During this interval, the wake function degradation of cognitive performance capacity continues as represented by S7d in FIG. 4(b). By preventing immediate accumulation of cognitive performance capacity at the beginning of a sleep period or following awakenings from sleep, this delay adjusts the cognitive performance capacity calculation S6b.

The delay of recuperation function is based upon empirical studies showing that the first few minutes of sleep are generally comprised of stage 1 sleep, which is not recuperative for sustaining cognitive performance capacity. Frequent arousals to wake or stage 1 sleep (sleep fragmentation) drastically reduce the recuperative value of sleep on cognitive performance capacity. Available data suggest that five minutes is the approximate length of time required to return to recuperative sleep (stage 2 or deeper sleep) following an arousal to wake or stage 1 sleep. If many hours of sleep are obtained without interruption, then the delays make only a small difference in overall restoration of cognitive performance capacity. If sleep is interrupted with frequent awakenings, the delays in recuperation after each awakening will accumulate, and thus substantially reduce total cognitive performance capacity restored during the total sleep period.

The delay function specifies the duration of a sleep interval during which application of the sleep function is postponed and a transitional formula is applied. A generalized form of the delay function for wake to sleep transitions is expressed as a decision rule:

$$d(t): \text{IF } (t - t_{LS}) \leq k_d$$

$$\text{THEN } C_t = d(t)$$

$$\text{ELSE } C_t = s(t) \qquad \text{Equation 6}$$

where LS stands for last state change, and thus the wake to sleep transition time $t_{LS}$ denotes the time of the last wake interval preceding a contiguous series of sleep intervals. This decision rule is shown in FIGS. 2 and 4(b) as S6b, S7c and S7d taken together. For calculating cognitive performance capacity during the interval $k_d$, cognitive performance capacity $C_t$ is evaluated by a transitional formula $C_t = d(t)$. After $k_d$ has elapsed, $C_t = s(t)$. Note that if wakefulness ensues before the end of $k_d$, then $C_t$ never reverts to s(t). That is the sleep function is not applied during the brief sleep interval.

It is believed that the preferred range for $k_d$ is from 0 to 30 minutes, more preferably $k_d$ equals about five minutes measured from the time of sleep onset before recuperation is derived from sleep. Preferably d(t) equals w(t). One of ordinary skill in the art will realize there are a variety of factors that influence the length of $k_d$. Thus a more preferred delay function may be expressed as:

$$d(t): \text{IF } (t - t_{LS}) \leq 5$$

$$\text{THEN } C_t = w(t)$$

$$\text{ELSE } C_t = s(t) \qquad \text{Equation 6a}$$

Figure 3A:
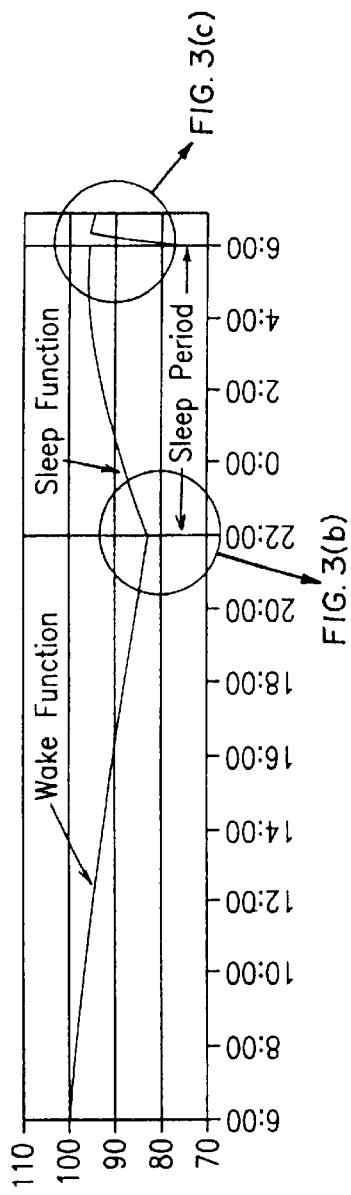
FIG. 3(a) graphically illustrates the effect of being awake and asleep on cognitive performance capacity over a 24-hour period.
Figure 3C:
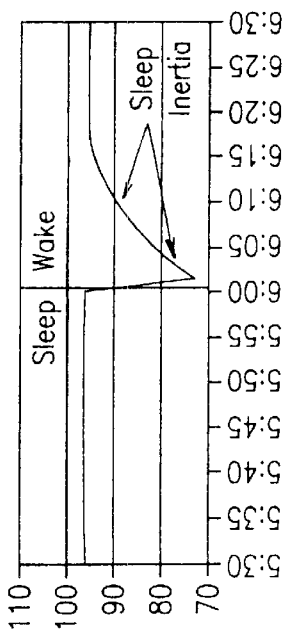
FIG. 3(c) is an enlarged view of circled portion 3(c) of FIG. 3(a), and graphically shows the sleep inertia function with respect to cognitive performance capacity.
Figure 3B:
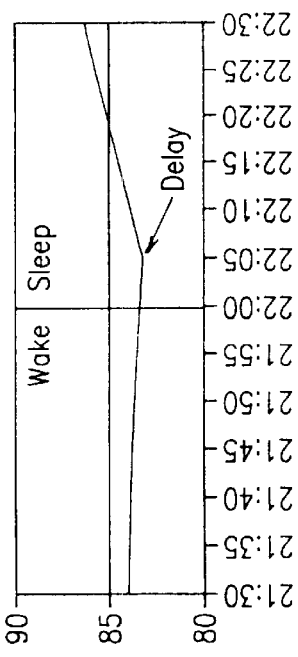
FIG. 3(b) is an enlarged view of circled portion 3(b) of FIG. 3(a), and graphically shows the delay function with respect to cognitive performance capacity.
Figure 4B:
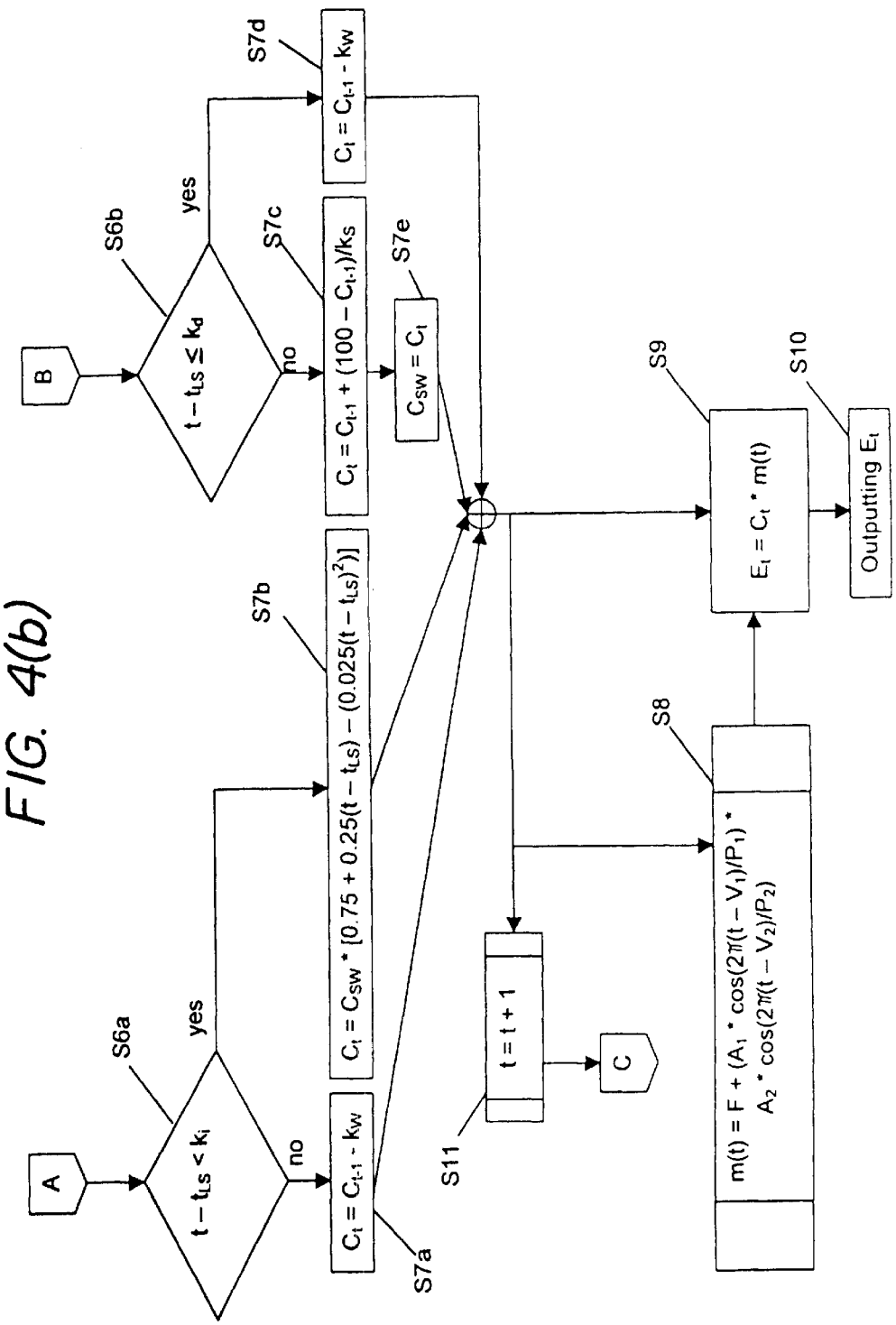

The effects of delayed recovery on cognitive performance capacity, as embodied by Equation 6a, are graphically illustrated in detail in FIG. 3(b).

As one of ordinary skill in the art will appreciate, PSG or similar scoring is able to classify when stage 1 sleep occurs. The conversion of PSG or similar scoring data would then convert the occurrences of stage 1 sleep into wake data for the sleep/wake history. Consequently, when the sleep/wake history is based on converted PSG or similar scoring data, the delay function d(t) is not necessary for the determination of an individual's cognitive performance capacity.

(4) Sleep Inertia Function i(t) for Sleep to Wake Transitions

The sleep inertia function i(t) defines the duration of an interval after awakening from sleep during which manifest cognitive performance capacity is suppressed below the actual current level. The sleep inertia function i(t) is based upon empirical data showing that cognitive performance is impaired immediately upon awakening, but improves primarily as a function of time awake. It is also based on positron emission tomography studies showing deactivated heteromodal association cortices (those areas that mediate this cognitive performance) immediately upon awakening from sleep, followed by reactivation of these areas over the ensuing minutes of wakefulness. That is, actual cognitive performance recuperation realized during sleep is not apparent immediately after awakening. The data indicate that 20 minutes is the approximate length of time required for cognitive performance capacity to return to levels that reflect actual recuperation accrued during sleep.

A sleep inertia delay value $k_i$ specifies the duration of the interval after awakening during which manifest cognitive performance capacity may be transitionally suppressed below the sleep-restored cognitive performance capacity level. During this interval, a transitional function bridges from an initial level to that determined by the wake function alone. A generalized form of the sleep inertia function for sleep to wake transitions is expressed as a decision rule:

$i(t)$: IF $(t-t_{LS})<k_i$

THEN $C_t=i(t)$

ELSE $C_t=w(t)$      Equation 7 where the sleep to wake transition time $t_{LS}$ denotes the time of the last sleep interval preceding a contiguous series of wake intervals. For calculating cognitive performance capacity during the interval $k_i$, $C_t$ is evaluated by a transitional formula $C_t=i(t)$. After $k_i$ has elapsed, $C_t=w(t)$. Equation 7 is represented in FIGS. 2 and 4(b) as S6a, S7a and S7b taken together.

The preferred range for $k_i$ is from 0 to about 60 minutes, and preferably in the range of about 10 to about 25 minutes, and most preferably between 18 and 22 minutes.

The sleep inertia function i(t) may be any function over the interval 0 to $k_i$, preferably any negatively accelerated function. A preferred sleep inertia function i(t) is a simple quadratic equation. This function preferably suppresses cognitive performance capacity by 10% to 25% immediately upon awakening, and most preferably by 25%. The function recovers 75% of the suppressed cognitive performance capacity in the first 10 minutes after awakening and 100% of the suppressed cognitive performance capacity usually by 20 minutes after awakening, after which the wake function resumes. These values are based on empirical data concerning the transition from sleep to wake. These studies show that cognitive performance is impaired immediately upon awakening from sleep, that the bulk of this impairment dissipates within the first few minutes of awakening, and that approximately 20 minutes is required for performance to be fully restored. Using the preferred 25% suppression of cognitive performance capacity and 20 minute recovery time, the preferred form of the sleep inertia function is expressed as a decision rule:

$i(t)$: IF $(t-t_{LS})<20$

THEN $C_t=C_{SW}*[0.75+0.025(t-t_{LS})-(0.025(t-t_{LS}))^2]$

ELSE $C_t=w(t)$      Equation 7a where $C_{SW}$ is cognitive performance capacity at the end of the sleep period calculated by the sleep function at the sleep to wake transition time $t_{LS}$. This decision rule is shown in FIGS. 2 and 4(b) as S6a, S7a, and S7b taken together. Equation 7a illustrates an initial suppression of 25% and $k_i$ equal to 20 minutes, and a negatively accelerated ramp bridging the interval until the wake function w(t) resumes its effects. The effect of the sleep inertia function i(t) on cognitive performance capacity, as embodied by Equation 7a, is graphically illustrated in FIG. 3(c).

An alternative variant of the sleep inertia function i(t) is a linear equation based on $k_i$ equal to 10 minutes and an initial 10% decrease in cognitive performance capacity. The resulting decision rule is then:

$i(t)$: IF $(t-t_{LS})<10$

THEN $C_t=C_{SW}*[0.9+(t-t_{LS})/100]$

ELSE $C_t=w(t)$      Equation 7b

As one of ordinary skill in the art will realize, both Equations 7a and 7b can be adjusted for a change in the value of $k_i$ and the initial suppression of cognitive performance capacity.

Second Step: Calculation of the Time of Day Modifier M

(1) Time of Day Function m(t)

The time of day function m(t) shown at S8 in FIG. 4(b) describes the cyclical 24-hour variation in cognitive performance. The time of day function m(t) is based on empirical data showing that under constant routine and/or total sleep deprivation conditions (i.e., with sleep/wake history controlled), cognitive performance capability oscillates between approximately 5% to approximately 20% peak to peak over a 24-hour period. This effect is commonly attributed to circadian rhythms of individuals. Output from this function modulates the current cognitive performance capacity prediction C (calculated in the first step) according to the time of day. The result of this modulation is the predicted cognitive performance capacity E. A generalized form of the time of day function is given by $M=m(t)$      Equation 8 where m(t) can be any rhythmic function with a base period of 24 hours, and, preferably, m(t) is the sum of two sinusoids, one with a period of 24 hours and the second with a period of 12 hours, which provides a biphasic circadian component. This function may be based on empirical data showing that a considerable proportion of variability seen in cognitive performance measurements can be accounted for by two such sinusoidal waveforms. As previously noted, the peak in empirically observed cognitive performance capacity occurs usually between 8:00 PM and 10:00 PM, and the trough occurs usually between 2:00 AM and 6:00 AM, providing a variation of approximately 5% to approximately 20% each day. A secondary trough occurs usually around 3:00 PM. Using these values for the preferred form of function m(t), the resulting function accounts for the empirically demonstrated asymmetry of daily cognitive performance rhythms, with a mid-afternoon decrease.

The descriptive form of the function m(t), including its offset and amplitude values varies with the operator selected for the third step. The computed value of the function can be expressed either as an additive percentage of cognitive capacity (dependent or independent of the current value of cognitive performance capacity $C_t$) or as a multiplicative dimensional scalar. The preferred form of the function, using the multiplicative operator, is expressed as $$m(t)=F+(A_1*\cos(2\Pi(t-V_1)/P_1)+A_2*\cos(2\Pi(t-V_2)/P_2)) \quad \text{Equation 8a}$$

where F is an offset, t is the time of day, $P_1$ and $P_2$ are periods of two sinusoids, $V_1$ and $V_2$ are the peak times of day in time units or epochs past midnight, and $A_1$ and $A_2$ are amplitudes of their respective cosine curves. This function may be used to modulate the previously calculated cognitive performance capacity C, the result being the predicted cognitive performance capacity E. Equation 8a is shown as S8 in FIGS. 1(a) and 4(b) and graphically illustrated as G8 in FIG. 1(b). As shown in FIG. 4(b), t is an input in the time of day function m(t) for each epoch of data.

For example in a preferred embodiment the variables are set as follows: t is the number of minutes past midnight, $P_1$ is equal to 1440 minutes, $P_2$ is equal to 720 minutes, $V_1$ is equal to 1225, and $V_2$ is equal to 560. Further, when $A_1$ and $A_2$ are represented as scalars, their amplitudes are in a range from 0 to 1, and more preferably are in a range from 0.01 to 0.2, and most preferably $A_1$ is equal to 0.082 and $A_2$ is equal to 0.036. Further in this example F is equal to either 0 or 1, and more preferably F is equal to 1. The resulting value of the time of day function m(t), in this example, is in the range of 0 to 2, and preferably in the range of 0.8 to 1.2, and most preferably in the range of 0.92 to 1.12.

Third Step: Calculation of Predicted Cognitive Performance

The overall process of calculating predicted cognitive performance capacity E is illustrated schematically in FIGS. 1(a)–(b) and 4(a)–(b). The time of day function M modulates the cognitive performance capacity C derived from the individual's sleep/wake history to generate the final predicted cognitive performance E as shown in FIGS. 1(a)–(b). In the third step, predicted cognitive performance E is derived from the combination of cognitive performance capacity C and time of day function M. In its most general form:

$$E=C\nabla M \quad \text{Equation 1}$$

where $\nabla$ is any mathematical operation for combining cognitive performance capacity C and time of day function M. The conventional choice of operations for providing this combination is addition or multiplication. Depending on the form of time of day function m(t) selected above, the same numerical value of predicted cognitive performance E can be generated by either operation. Most preferably the combination is performed with multiplication S9, represented as:

$$E=C*M \quad \text{Equation 1a}$$

In Equation 1a, the predicted cognitive performance E is the modulation of the current cognitive performance capacity C and a value centered around the number one representing the current value of the time of day modulator M.

As noted above, the preferred numerical representation of cognitive performance capacity C is a value ranging from zero to 100 to represent a percentage of cognitive performance capacity available. However, predicted cognitive capacity E can meaningfully exceed 100 under certain circumstances due to time of day modulation about the current value of cognitive performance capacity C. A possible example of such a circumstance would be a sleep period resulting in 100% cognitive performance capacity C and terminated at the evening peak (and after sleep inertia has dissipated). To retain the 100% scale, either the predicted cognitive capacity E may be truncated/clipped at 100% or 0 to 120% may be scaled to 0 to 100%. Either choice will maintain a maximum of 100%. This most likely will be implemented as scaling 120% to 100% and then truncating/clipping any predicted cognitive capacity E to 100%.

As shown in FIG. 1, the method repeats for each new epoch of data. For each iteration of the method, one time unit equal to the length of an epoch may be added to time t preferably in the form of a counter S11 as exemplified in FIG. 1.

In the preferred embodiment described above, the sleep inertia function i(t) is applied to cognitive performance capacity C prior to modulation of cognitive performance capacity C by the time of day modifier M. An alternative embodiment applies the sleep inertia function i(t) not to cognitive performance capacity C, but to predicted cognitive capacity E, that is, subsequent to the modulation of cognitive performance capacity C by time of day modifier M. The state of empirical knowledge is insufficient to determine whether the preferred embodiment is better than this alternative embodiment.

Also in the preferred embodiment described above, the wake function w(t) is set to zero when the sleep inertia function i(t) is applied. Another alternative embodiment applies the sleep inertia function i(t) and the wake function w(t) simultaneously. When the sleep inertia function i(t) and the wake function w(t) become equal to each other or the sleep inertia function i(t) becomes greater than the wake function w(t), then cognitive performance capacity C is calculated using the wake function w(t).

Figure 5:
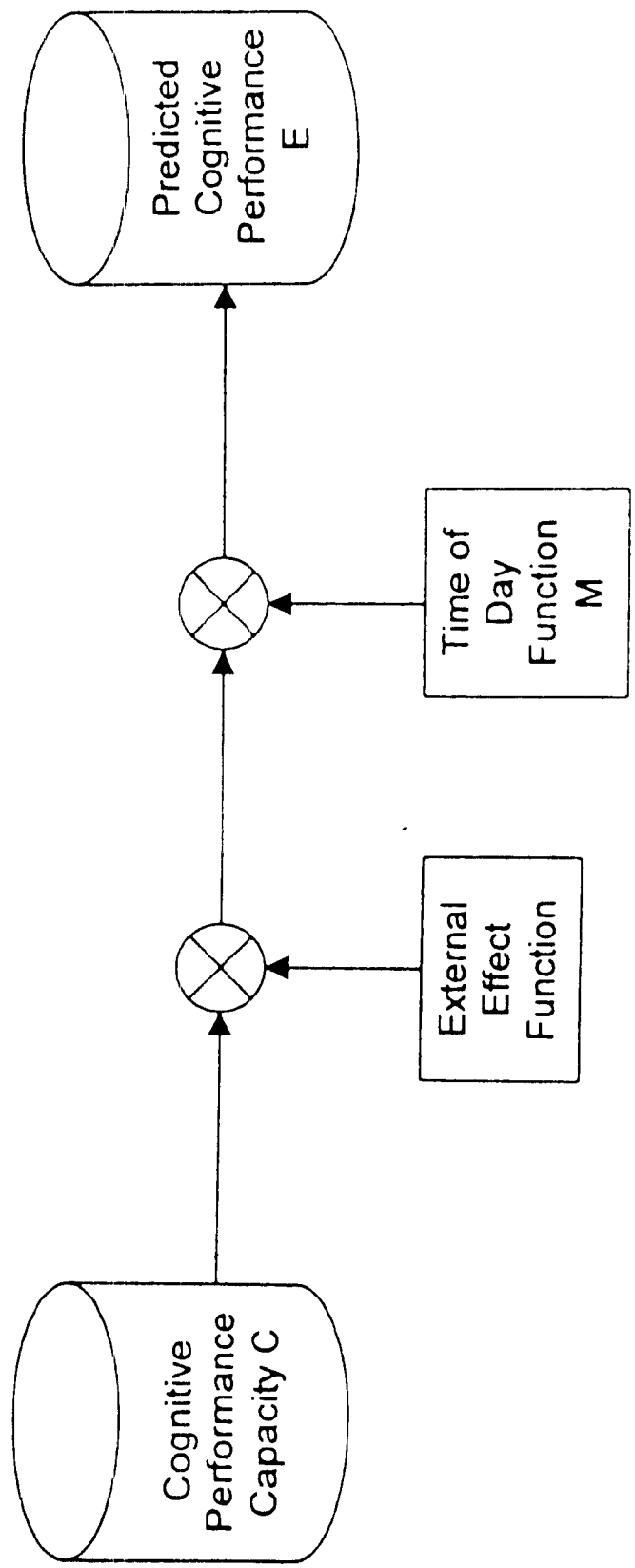
FIG. 5 illustrates a functional representation of an alternative embodiment.

The preferred embodiment may be further modified to account for the effects of narcotics or other influences that will impact the cognitive capacity as shown in FIG. 5. Further modification to the preferred embodiment will allow for the inclusion of jet lag and similar time shifting events by, for example, compressing or expanding the 24 hour period of the time of day function M(t) over a period of days to realigning the time of day function M(t) to the adjusted schedule.

IMPLEMENTATION OF THE METHOD

The preferred embodiment may be realized as software to provide a real-time current state of an individual's cognitive performance and the capability upon demand to extrapolate future levels of cognitive performance. A flowchart representing the steps to be performed by the software in the preferred embodiment is shown in FIGS. 4(a)–(b) and for an alternative embodiment, to be described later, in FIGS. 7(a)–(b).

The software may be implemented as a computer program or other electronic device control program or an operating system. The software is preferably resident in a device, e.g. an actigraph, attached to the individual or in a stand-alone device such as a personal computer, a PAL device, a personal digital assistant (PDA), an e-book or other handheld or wearable computing devices (incorporating Palm OS, Windows CE, EPOC, or future generations like code-named products Razor from 3Com or Bluetooth from a consortium including IBM and Intel), a specific purpose device receiving signals from a device, e.g. an actigraph, attached to an individual or human input from human analysis or observation. The software could be stored, for example, in random access memory (RAM); in read only memory (ROM); on a storage device like a hard drive, disk, compact disc, punch card, tape or other computer readable material; in virtual memory on a network, a computer, an intranet, the Internet, the Abilene Project, or otherwise; on an optical storage device; on a magnetic storage device; and/or on an EPROM. The software may allow for the variables in the equations discussed above to be adjusted and/or changed. This capability will allow users to adjust the variables based on empirical knowledge and also learn the interrelationship between the variables.

The software implementation onto the measuring device such as an actigraph will convert any decimal numbers used in calculations into integers that are appropriately scaled as is well known to those skilled in the art. Further the integers would then be approximated such that minimal error would be created, for example, approximation for the Cole-Kripke algorithm weighting factors become 256, 128, 128, 128, 512, 128, and 128, respectively. Using linear approximation will simplify the binary arithmetic and the corresponding assembly code for software implementation.

In software, the time of day modulator would be embodied as a table with one hour steps resulting in 24 rows using 8-bit unsigned integers. The intervening steps would be interpolated from the one hour steps to provide 15-minute steps. This simplification provides sufficient resolution for available displays. As the resolution of available displays improves, smaller temporal steps may be used for the table and/or interpolation to replicate the time of day modulator. A pointer system would be utilized to retrieve the appropriate data to calculate the time of day modulator. Depending on a myriad of factors, one of ordinary skill in the art will most likely choose a multiplicative modulation to achieve appropriate scaling or an additive modulation for less complex but more rapid evaluation, i.e., if speed is a concern. The main disadvantage with the additive modulation is that there will be an approximately 3% error compared to the 1% error using the multiplicative modulation in this invention. This system will allow the time of day function to be uploaded when the actigraph is initialized and reduce the repetitive computational burden that would exist if a cosine table was used and the time of day function was calculated from the cosine table for each epoch.

Figure 6:
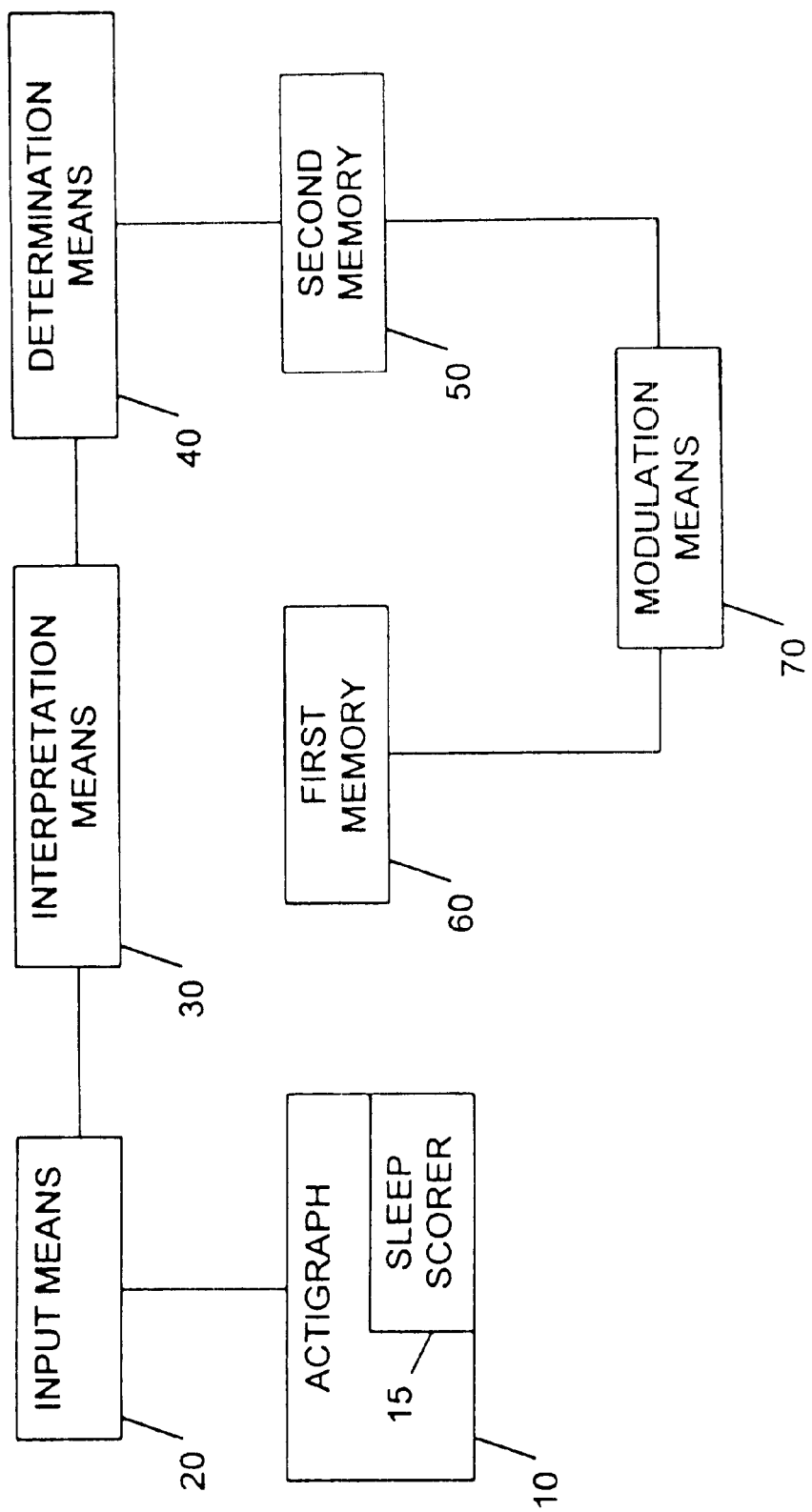
FIG. 6 depicts a block diagram of structural components for the preferred embodiment.

The preferred embodiment, as shown in FIG. 6, may also be realized by a stand-alone device or a component add-on to a recording device. The stand-alone device is separate from the device or other means of recording an individual's sleep history. In contrast, the component add-on to a recording device includes modifying the recording device to include the component add-on to provide one device that both records and analyzes an individual's sleep history.

A suitable stand-alone device includes a physical input connection, e.g., an input port (input means 20) to be physically connected to an input device, e.g., a keyboard, data entry device, or a data gathering device such as an actigraph. Alternatively, the physical connection may occur over an information network. Alternatively, the physical input connection may be realized by a wireless communication system including telemetry, radio wave, infrared, PCS, digital, cellular, light based system, or other similar systems. The wireless communication system has an advantage in that it eliminates the need for a physical connection like cables/wires, plug-ins, etc. which is particularly convenient when monitoring a mobile subject. The data gathering or data entry device provides a sleep history that may include past, present and/or predicted/anticipated sleep patterns of an individual. Input means 20 embodies S1 for initial inputting of information and S2 for the continual or one-time loading of data depending upon the implementation selected.

The stand-alone device further includes a data analyzer (interpretation means 30). The data analyzer performs S3–S6b. Interpretation means 30 analyzes the input data by performing different analysis functions. Interpretation means 30 compares the present input data to the last input data to determine if there has been a change from sleep to wake or wake to sleep; and if so, then set a time counter to the time for the last state, S3 and S4a in FIG. 4(a). Interpretation means 30 also classifies the inputted data, as represented by S5 in FIG. 4, to then be able to select or generate at least one of the following calculation functions responsive to the composition of the input data: 1) wake function, 2) sleep function, 3) delay function, and 4) sleep inertia function as depicted by S6a–S7d in FIG. 4(b). Interpretation means 30 may be realized by an appropriately programmed integrated circuit (IC). One of ordinary skill in the art will realize that a variety of devices may operate in concert with or be substituted for an IC like a discrete analog circuit, a hybrid analog/IC or other similar processing elements.

The stand-alone device further includes a calculator (determination means 40). Determination means 40 may be implemented by appropriately programming the IC of the interpretation means or it may be implemented through a separate programmed IC. Determination means 40 calculates the cognitive performance capacity factoring in the sleep/wake history and the current state using the function selected by interpretation means 30, S7a–S7d in FIG. 4(b).

The interpretation means 30 and determination means 40 may be combined into one combined means or apparatus.

The stand-alone device further includes a first memory 60 that stores modulation data including a modulating data series or curve preferably representing a time of day curve. The stand-alone device further includes a second memory 50 that holds data for the creation of a data series or a curve representing cognitive performance capacity C over time t. The first memory 60 and the second memory 50 may be any memory known to those of ordinary skill in the art. The second memory 50 is preferably a first-in-first-out memory providing means for adding the value from the determination means 40 to the end of the data series or the curve. The first memory and the second memory may be combined as one memory unit. As one of ordinary skill in the art will realize there may be a memory to store the various intermediary values necessary for calculating cognitive performance capacity C and predicted cognitive performance E as required to implement this invention as either hardware or software.

The stand-alone device also includes, as a separate IC or in combination with one of the previously mentioned ICs, a modulator (modulation means 70) embodying S8–S9 shown in FIG. 4(b). Modulation means 70 receives the present cognitive performance capacity calculated by determination means 40 and calculates the time of day value from data stored in the first memory 60. Modulation means 70 modulates the first data series or curve (cognitive performance capacity) with the time of day value. The modulation preferably is performed by matching the timing sequence information relating to the data series or the curves based on the latter of midnight and the length of time from the initial input of data as preferably determined by the number of epochs and the initial starting time related to the first entered sleep/wake state. Modulation means 70 may modulate a series of cognitive performance capacity values with the time of day function if the second memory 50 exists to store the cognitive performance capacity values.

As is well known by one of ordinary skill in the art, a counter or other similar functioning device and/or software coding may be used in the stand-alone device to implement S11 shown in FIG. 4(b).

The stand-alone device may also include a display to show a plotted modulated curve representing the modulation result over time, as stored in a memory, e.g. a first-in-first-out memory, or a numerical representation of a point on the modulated curve at a selected time from the modulation means 70 representing the predicted cognitive performance E. The numerical representation may take the form of a gauge similar to a fuel gauge in a motor vehicle. The stand-alone device, as an alternative or in addition to the display, may include a printer or communication port to communicate with an external device for printing and/or storage of a representation of predicted cognitive performance E.

The stand-alone device instead of having dedicated hardware may provide the storage space and processing power to execute a software program and accompanying data files. In this case, the stand-alone device may be a desktop computer, a notebook computer, or similar computing device. The software program handles the receiving of the data representing sleep history from an outside source through a communication port or via a computer network such as intranets and the Internet, and then performs the necessary analysis and processing of the method described herein. The storage space may be a memory in the form of computer readable material storing at least the time of day curve and possibly the input data, which may also be resident in the random-access-memory (RAM) of the computer given its temporary use. The input data and the resulting produced data indicating various cognitive performance levels of an individual may also be saved to a more permanent memory or storage than is available in RAM.

An alternative embodiment modifies the input port 20 to receive some form of raw data, i.e., prior to being sleep scored, representing sleep activity of an individual. In this embodiment, the interpretation means 30 would then sleep score the raw data as part of the data analysis performed by it. A third memory to store the weighting factors required for sleep scoring, if a table is used for them, else the sleep scoring function will implicitly include the weighting factors and the third memory will be unnecessary.

Another alternative embodiment provides for the interpretation means 30 to filter the sleep/wake data such that for the first $k_d$ number of sleep epochs after a wake epoch are changed to wake epochs. In keeping with the invention, the filtering may be accomplished a variety of ways. The preferred way is to add a decision step prior to S3 in FIG. 4(a) such that if $D_{SW}$ is a sleep epoch and $t-t_{LS}<k_d$, then S3–S6a will be skipped and S7a will occur. The result is that the decision rule represented as d(t) in Equation 6 above would be eliminated, and S6b and S7d would be unnecessary in FIGS. 4(b) and 7(b).

One of ordinary skill in the art will appreciate that the stand-alone device is broad enough to cover a computer/workstation connected to the Internet or other computer network. A user would transmit their sleep/wake history over such network to the stand-alone device for obtaining a predicted cognitive performance based on the transmitted data. The interface of the stand-alone device may allow the user to adjust the variables discussed above in connection with the method to learn the interrelationship between the variables and the predicted cognitive performance. Preferably, the range of allowable adjustment of the variables would be that of the respective ranges discussed in connection with each of the variables above.

The component add-on to the measuring device may have similar components to the stand-alone device described above and shown in FIG. 6. Preferably the component add-on is contained in one integrated chip to minimize the space needed to house it and/or is implemented as software as part of a designed measuring device. However, the add-on component may include more than one electrical component, e.g., a memory chip and an IC. The component add-on may transmit the predicted cognitive performance to a remote device for further analysis.

Both the software and hardware are envisioned as being able to operate and function in real-time. For the purposes of this invention, real-time is understood to represent a continuous stream and analysis of cognitive performance level for each epoch of sleep/wake data entered. Thus, the software and hardware will both provide to an individual or some other entity the present cognitive performance level based on the data from the last entered epoch of sleep/wake data entered into either the software or hardware. Most sleep scoring systems make the sleep/wake determination based on data from epochs on either side of the epoch being analyzed. Consequently, there is a delay in providing information to the user.

As one of ordinary skill in the art will appreciate from the following discussion, the described method is able to accept a continuous stream of data from either individual epochs or groups of epochs. If blocks of time are entered, then after initial transitions the first few epochs are governed by the appropriate transition function with the appropriate time of solid sleep or wakefulness being used in the non-transition functions.

As a feature of the invention, the sleep/wake data may comprise the time at which a state change occurs from sleep to wake or wake to sleep. The sleep/wake data may also comprise the duration of the individual's wake state and the duration of the individual's sleep state. In order to generate the predicted cognitive performance curve, the sleep/wake data may be extrapolated and/or expanded into a series of individual epochs. As discussed above an epoch represents a predetermined length of time. Thus the sleep/wake data may be presented in conventional units of time or may be presented in epochs. For example, if the sleep/wake data was sleep for 10 epochs and wake for 3 epochs, in generating the cognitive performance capacities, epochs 1 through 10 may represent the sleep state and epochs 11 through 13 may represent the wake state.

In accordance with an aspect of the invention, the predicted cognitive performance E at a particular time q may be determined using either the predicted cognitive performance E or the cognitive performance capacity C at time r as a base point where r can be before or after time q. From the base point determining the cognitive performance capacities for the time points between times q and r where there is a change in state.

Figure 7A:
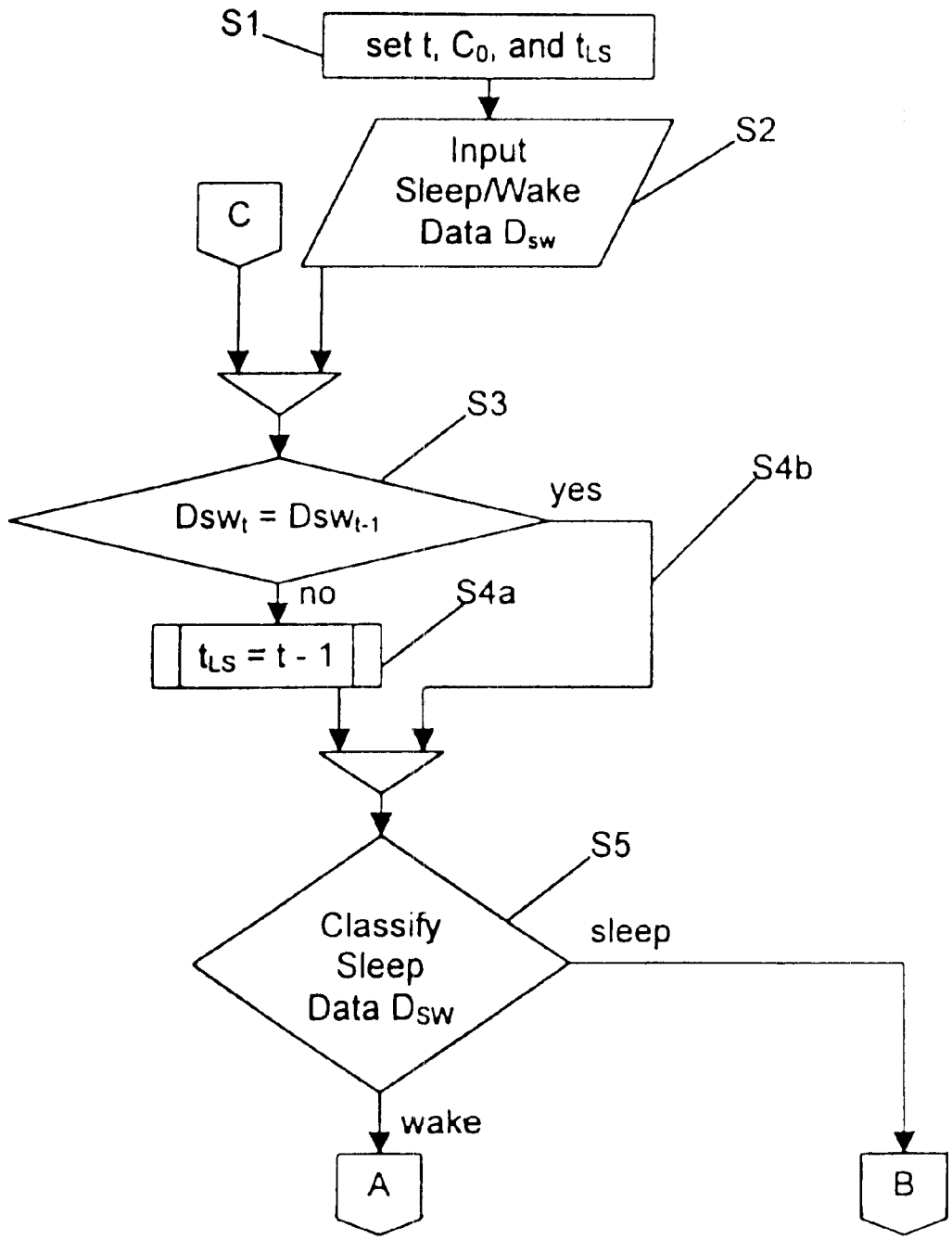
FIGS. 7(a)–(b) illustrate a detailed flowchart showing the steps of an alternative embodiment.
Figure 7B:
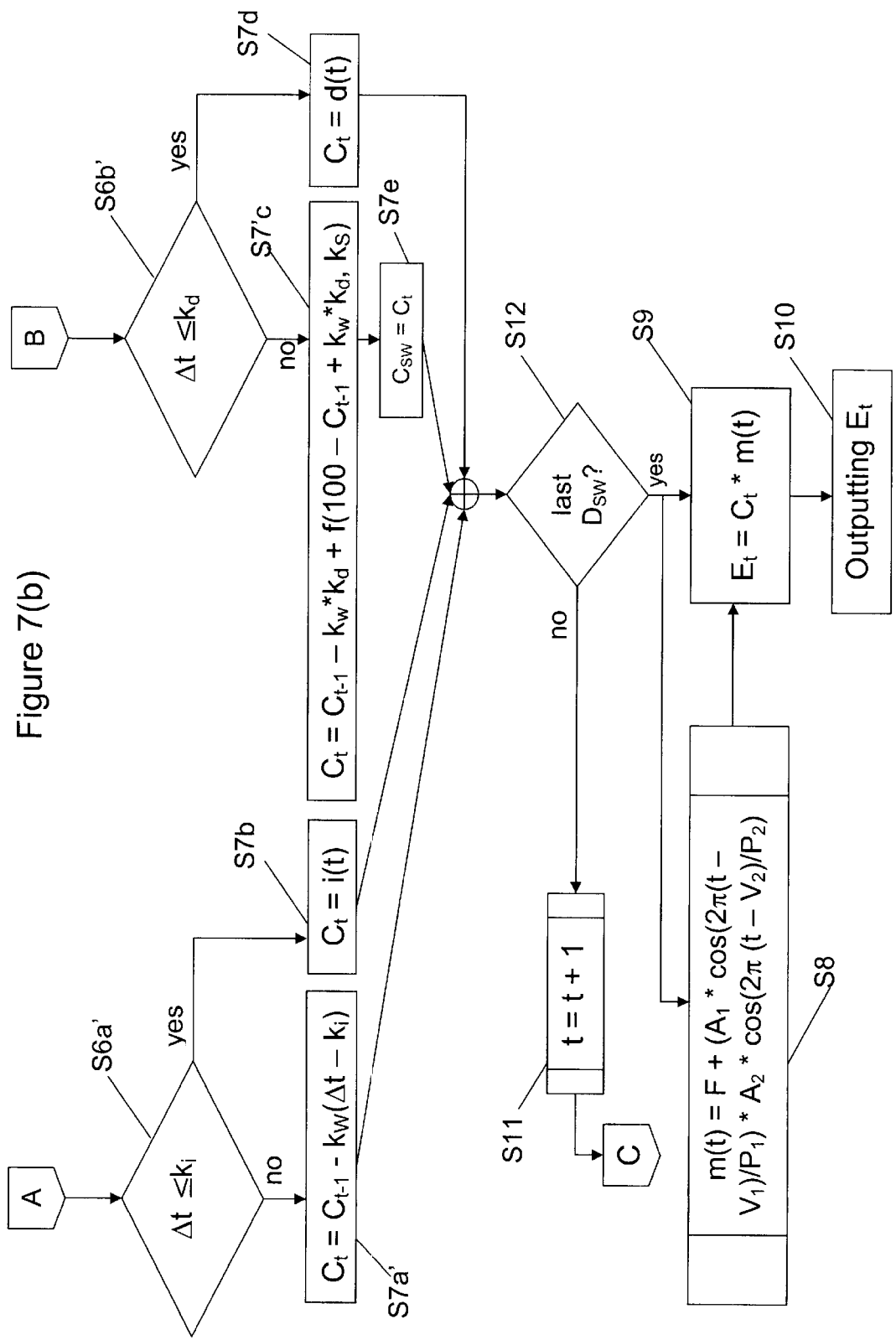

As shown in FIGS. 7(a)–(b), the steps are substantially the same as the preferred embodiment with changes made to the wake and sleep functions, consequently the definition of the variables is the same as the preferred embodiment except as noted. The equations described below and the steps shown in FIGS. 7(a)–(b) are for the situation when the initial cognitive value is prior in time to the desired predicted cognitive value. Each element of sleep/wake data is classified as either sleep or wake.

If the sleep/wake data represents the wake state, then a selection is made between two functions as to which is applicable based on the following decision rule:

IF $\Delta t \leq k_i$

THEN $C_t = i(t)$

ELSE $C_t = w_m(t)$   Equation 10 where $\Delta t$ represents the amount of time in the current state, i.e., $t - t_{LS}$. The sleep inertia function $i(t)$ is used only if the last data entry is the wake state for a period of time is less than or equal to $k_i$. Thus the same sleep inertia function $i(t)$ as used in the preferred embodiment is also used in this alternative embodiment. The modified wake function $w_m(t)$ takes into account that the sleep inertia function $i(t)$ provides a delay of $k_i$ when a curve is formulated, such that after an individual recovers from the initial suppression of cognitive performance capacity the individual returns to the level of cognitive performance capacity of the last epoch the individual was asleep prior to waking. Accounting for this delay provides the following:

$$w_m(t) = C_{t-1} - k_w(\Delta t - k_i)$$   Equation 11

If the sleep/wake data represents the sleep state, then a selection is made between two functions as to which is applicable based on the following decision rule:

IF $\Delta t \leq k_d$

THEN $C_t = d(t)$

ELSE $C_t = s_m(t)$   Equation 12

The delay function $d(t)$ is used only if the last data entry is the sleep state for a period of time is less than or equal to $k_d$. Thus the same delay function $d(t)$ as used in the preferred embodiment is also used in this alternative embodiment. The modified sleep function $s_m(t)$ takes into account the delay function for a period of time equal to $k_d$. Accounting for the delay function $d(t)$ provides the following:

$$s_m(t) = ((C_{t-1} - (k_w * k_d)) + (100 - (100 - C_{t-1})(1 - 1/k_s)^{\Delta t - kd})$$   Equation 13 where the first part of the equation represents the delay function $d(t)$ and the second part represents the recovery of cognitive performance capacity C.

A summation of the time components of the sleep/wake data is performed as each piece of sleep/wake data is handled with respect to the calculation of the cognitive performance capacity or prior to modulation of the final cognitive performance capacity with the time of day function $m(t)$. The latter is shown in FIGS. 7(*a*)–(*b*). After the new cognitive performance capacity $C_t$ is calculated, the method repeats to handle the next piece of sleep/wake data if the present piece is not the last piece. After the last piece the predicted cognitive performance E is calculated based on Equation 1 above and as detailed in the preferred embodiment.

It should be noted again that this method includes the processes and calculations based on Equations 1 through 8 expressed in their general form. Embodiments shall apply functions relating the variables involved according to empirical knowledge, resulting in specific expressions of those equations, as illustrated in the text and FIGS. 1–4(*b*) above (but not confined to these), which may be changed or refined according to the state of empirical knowledge.

APPLICATIONS OF THE METHOD

For the discussions that follow about FIGS. 8–17, the predicted cognitive performance E (i.e., the combination of cognitive performance capacity C and time of day function M) is plotted as a continuous line across multiple days. The darker sections of the line indicate sleep periods and the lighter sections of the line indicate wake periods. Predicted cognitive performance E is illustrated on a scale of 0 to 120%. Using the preferred embodiments, predicted cognitive performance E can theoretically reach 120%, but only when cognitive performance capacity C is 100% (i.e., 20 minutes after awakening from a sleep period in which cognitive performance capacity C was fully restored) and simultaneously the time of day function M is at its acrophase. Although possible, in practice this situation is unlikely. For purposes of illustration and description, "acceptable" predicted cognitive performance E is set at 85%. This value represents the approximate percent decrement in predicted cognitive performance E after 16 hours of continuous wakefulness when preceded by 8 hours of nighttime sleep (i.e., a typical sleep/wake schedule). Temporal resolution along the abscissa of the illustrations is one hour per vertical tick mark. Major vertical gridlines correspond to 0:00 AM (midnight) local time.

(1) Impact of Idealized Sleep on Predicted Cognitive Performance E

In its simplest application, the method according to the invention may be used to predict the impact of various idealized (i.e., unfragmented) amounts of nightly sleep on predicted cognitive performance E. For this exercise, the individual obtains eight hours of unfragmented sleep per night for the first night. Next, the individual obtains 8 (FIG. 8) or 4 (FIG. 9) hours of unfragmented sleep per night. Then the individual again obtains eight or four hours, respectively, of unfragmented sleep.

Figure 8:
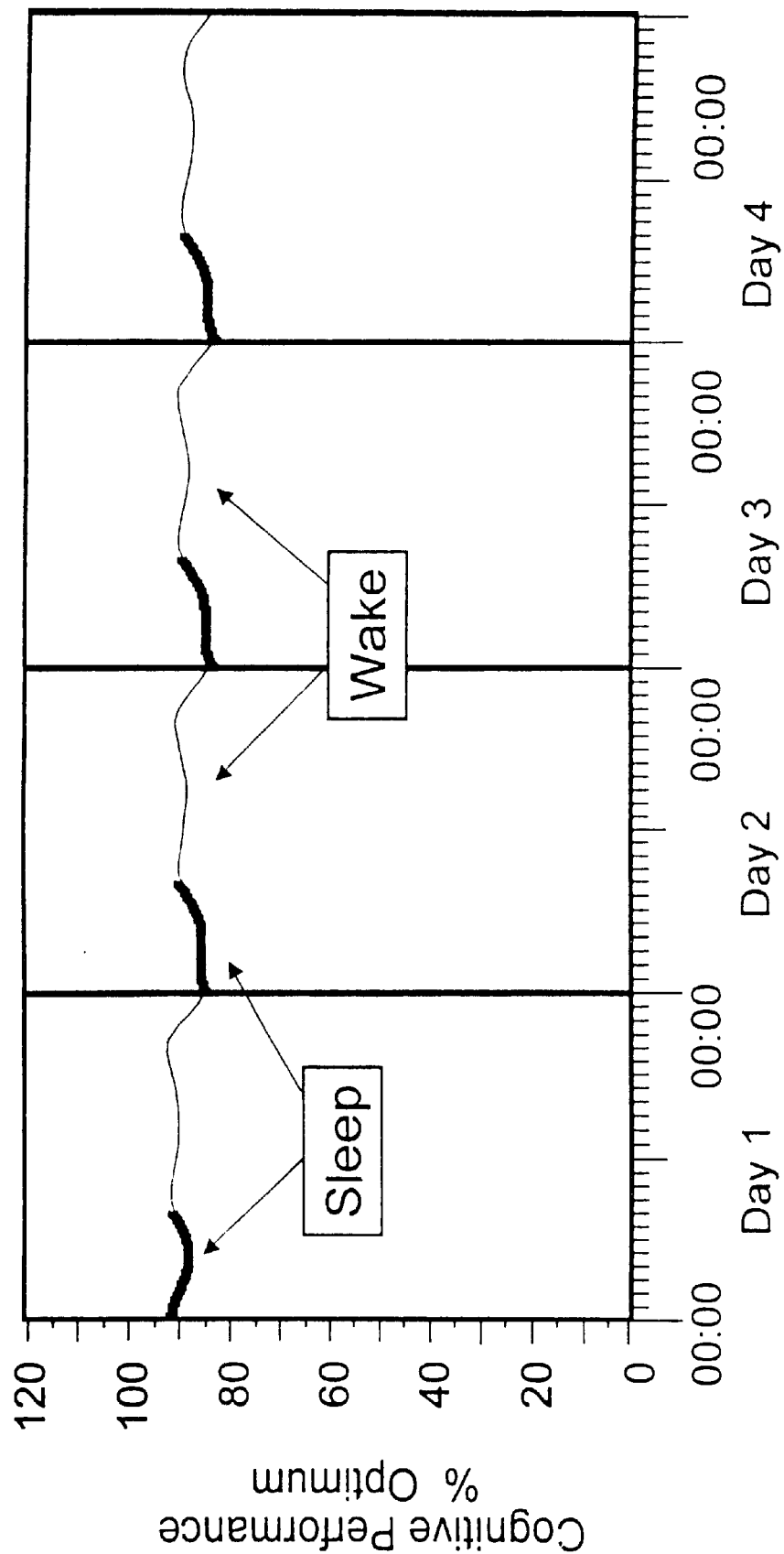
FIG. 8 illustrates predicted cognitive performance with 8 hours of sleep per night.
Figure 9:
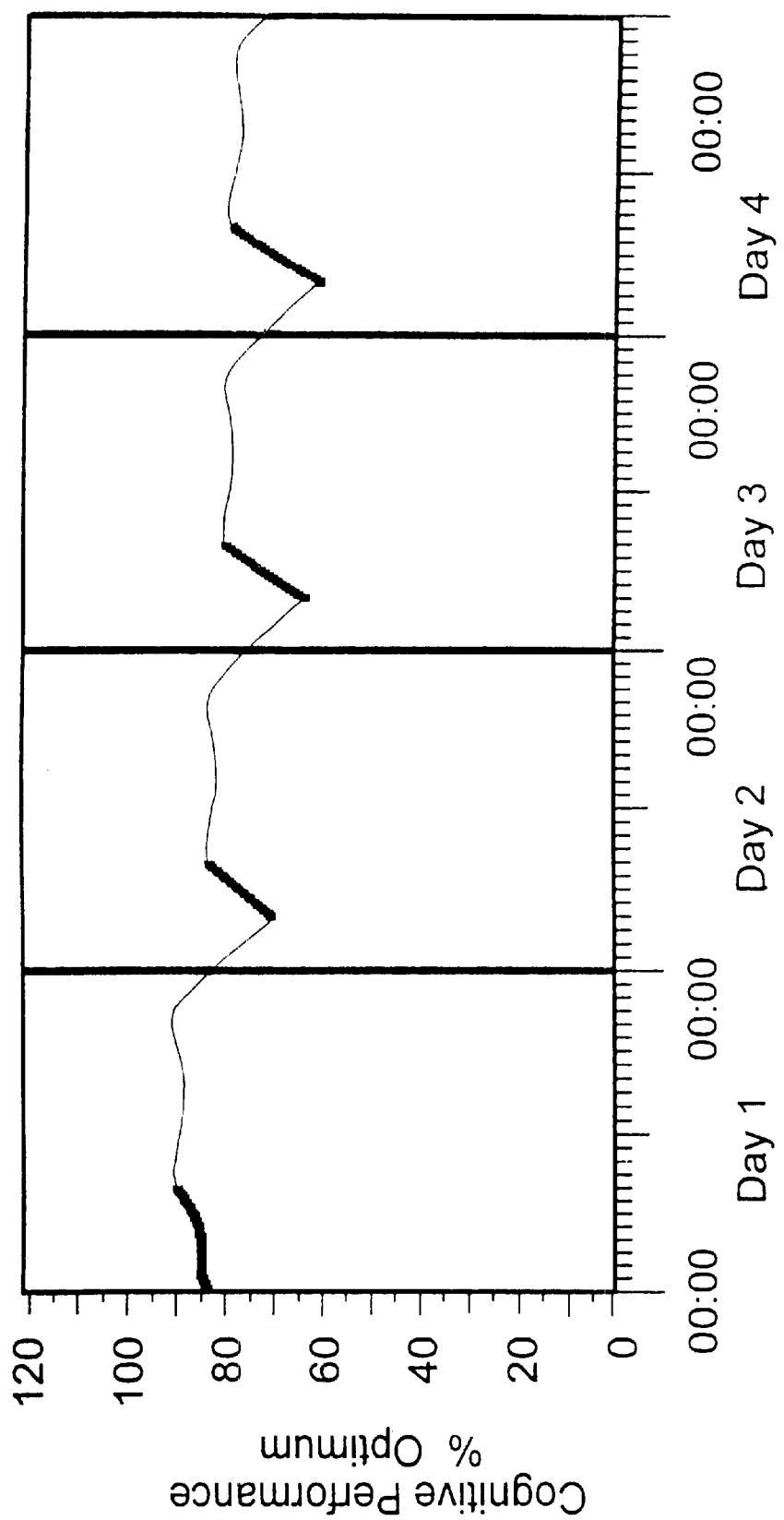
FIG. 9 illustrates predicted cognitive performance with 4 hours of sleep per night.

As illustrated in FIG. 8, the method predicts that with eight hours of sleep per night, acceptable predicted cognitive performance E is maintained across waking hours, dropping only slightly below 85% for the 40 minutes preceding sleep onset each day. As illustrated in FIG. 9, for sleep amounts of four hours per night, the method predicts that after the first night of restricted sleep, predicted cognitive performance E falls below acceptable levels for the entire waking period. Furthermore, because of the restricted sleep period, predicted cognitive performance E is not completely restored each night, despite the higher rate of accumulation of cognitive performance E during sleep.

Figure 10:
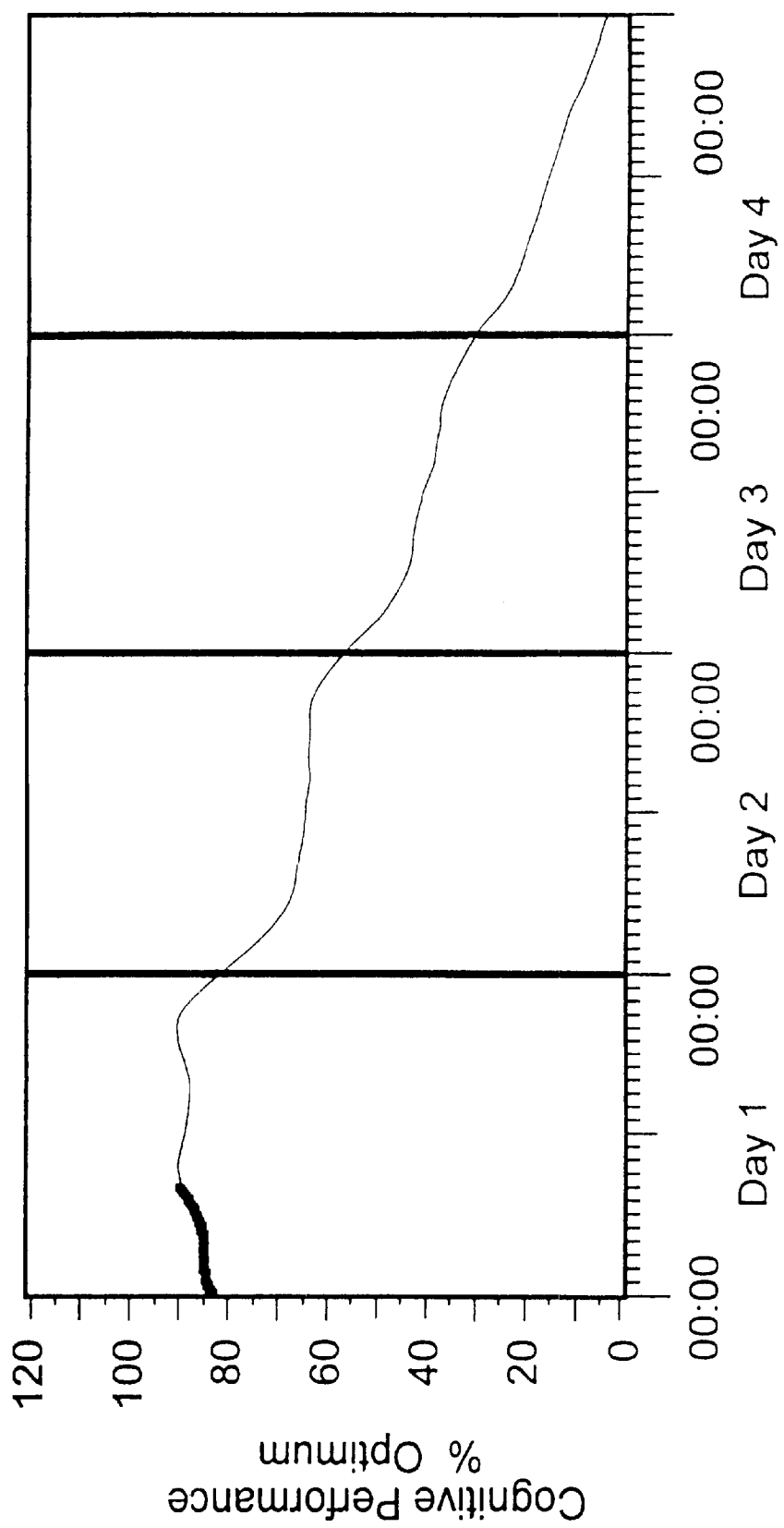
FIG. 10 illustrates predicted cognitive performance with no sleep during 72 hours of total sleep deprivation.
Figure 11:
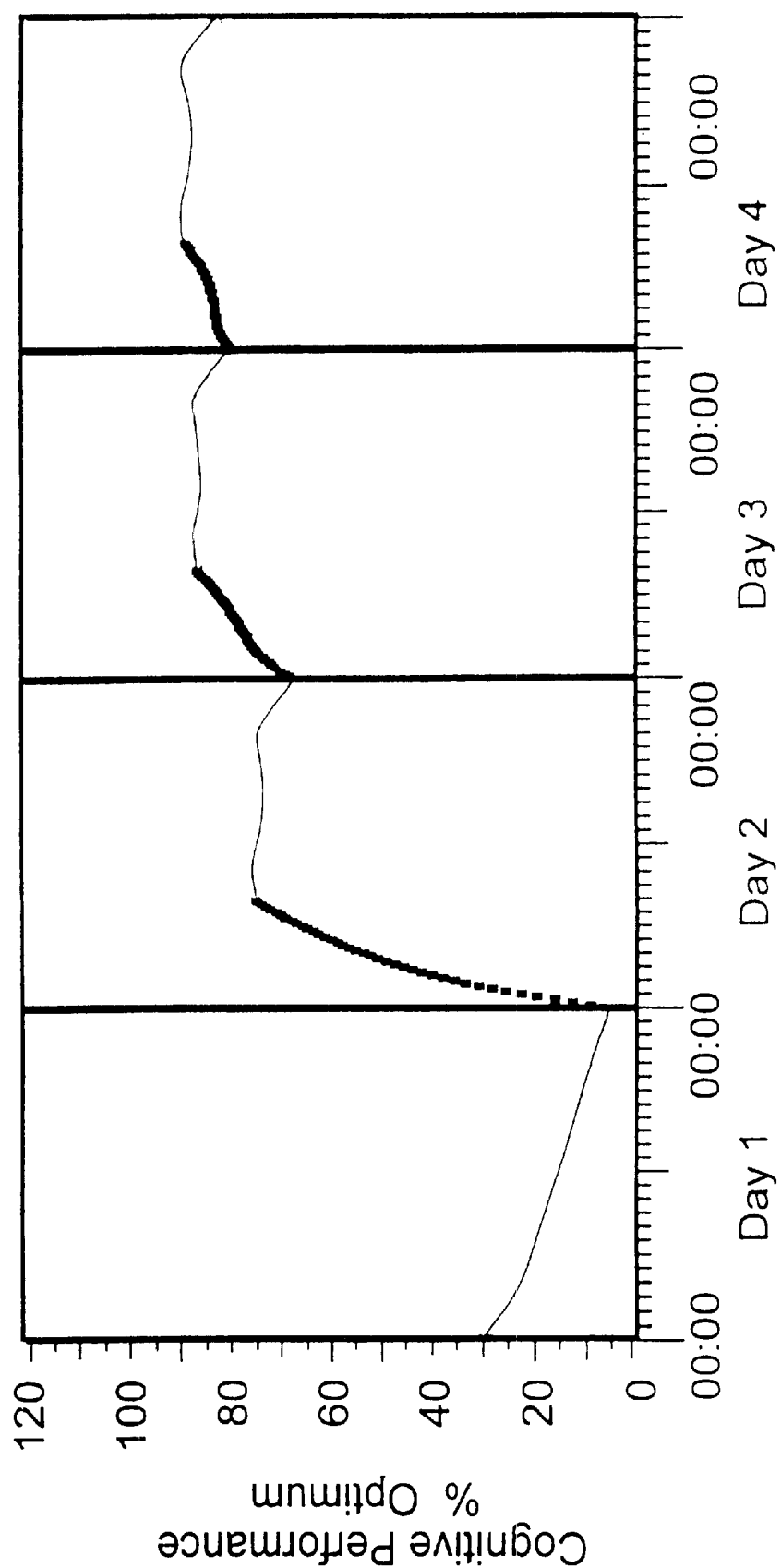
FIG. 11 illustrates predicted cognitive performance with a recovery sleep of 8 hours the night after total sleep deprivation.

Under conditions of total sleep deprivation illustrated in FIG. 10 commencing on night 2, the method predicts that predicted cognitive performance E falls to near-zero levels on Day 4 after 88 hours awake. The predicted rate of cognitive performance E accumulation during recovery sleep is shown in FIG. 11. This steep rate of accumulation on the first night (Day 2) of recovery sleep is a result of the near-complete depletion of predicted cognitive performance E. However, in spite of this steep rate, predicted cognitive performance E accumulation is not complete (above the arbitrary 85% "acceptable" level) until after the second night (Day 3) of recovery sleep. Likewise, the rate of accumulation on the second night of recovery sleep is slightly lower than the rate on the first night of recovery sleep, due to the lower level of preceding sleep debt (and correspondingly higher level of predicted cognitive performance E) at sleep onset.

Figure 12:
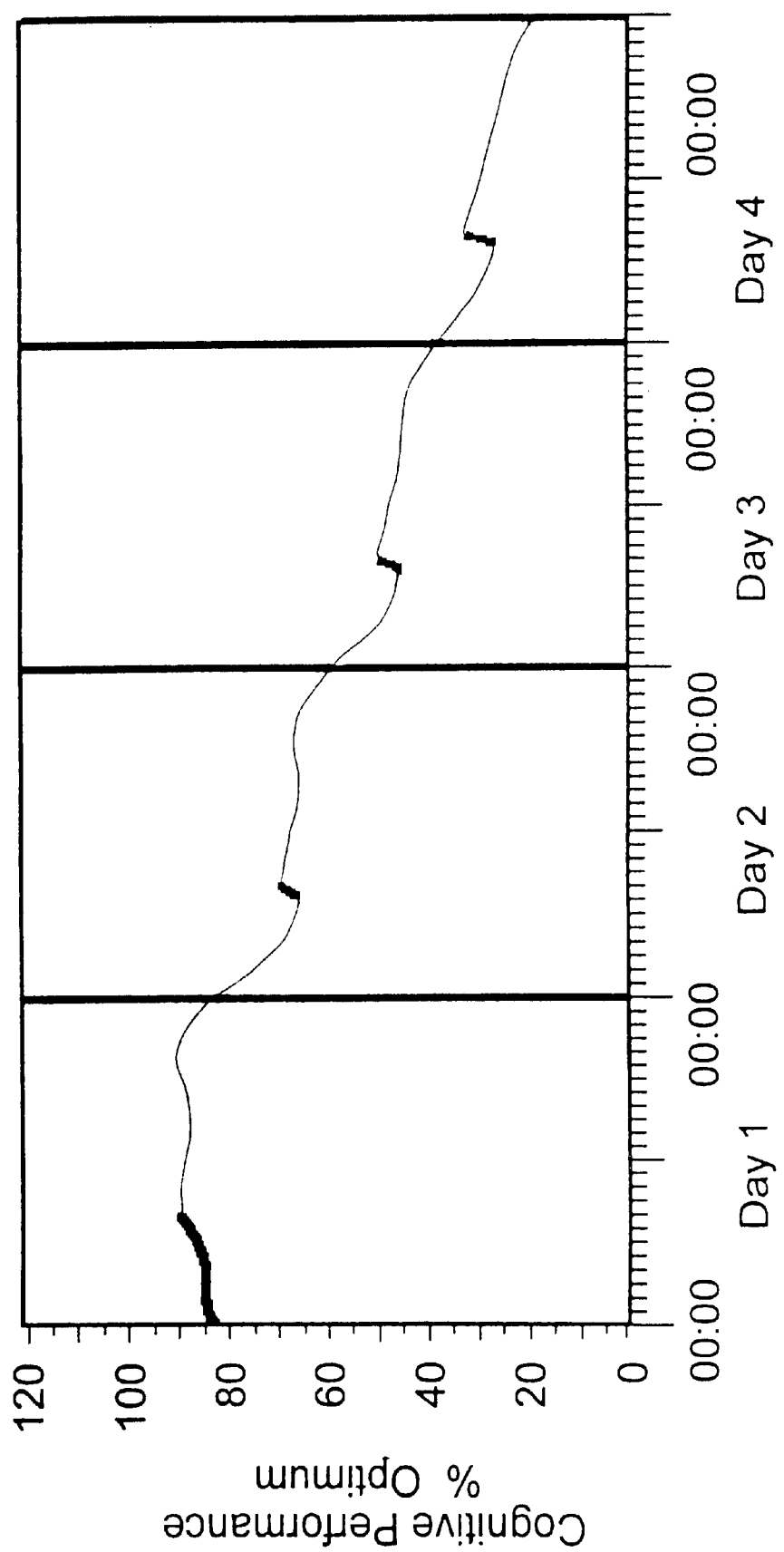
FIG. 12 illustrates predicted cognitive performance with daily 30-minute naps during 85 hours of sleep deprivation.

The impact of a near-complete depletion of predicted cognitive performance E on the rate of predicted cognitive performance E accumulation during sleep is illustrated in FIG. 12. This figure shows predicted cognitive performance E across 3.5 days of sleep deprivation in which a daily 30-minute sleep period occurs on Days 2–4. The rate of accumulation during the 30-minute sleep period is nearly vertical. Although predicted cognitive performance E declines both within and across each day, it is substantially offset by the 30-minute sleep period.

(2) Impact of Sleep Fragmentation on Predicted Cognitive Performance E

Figure 13:
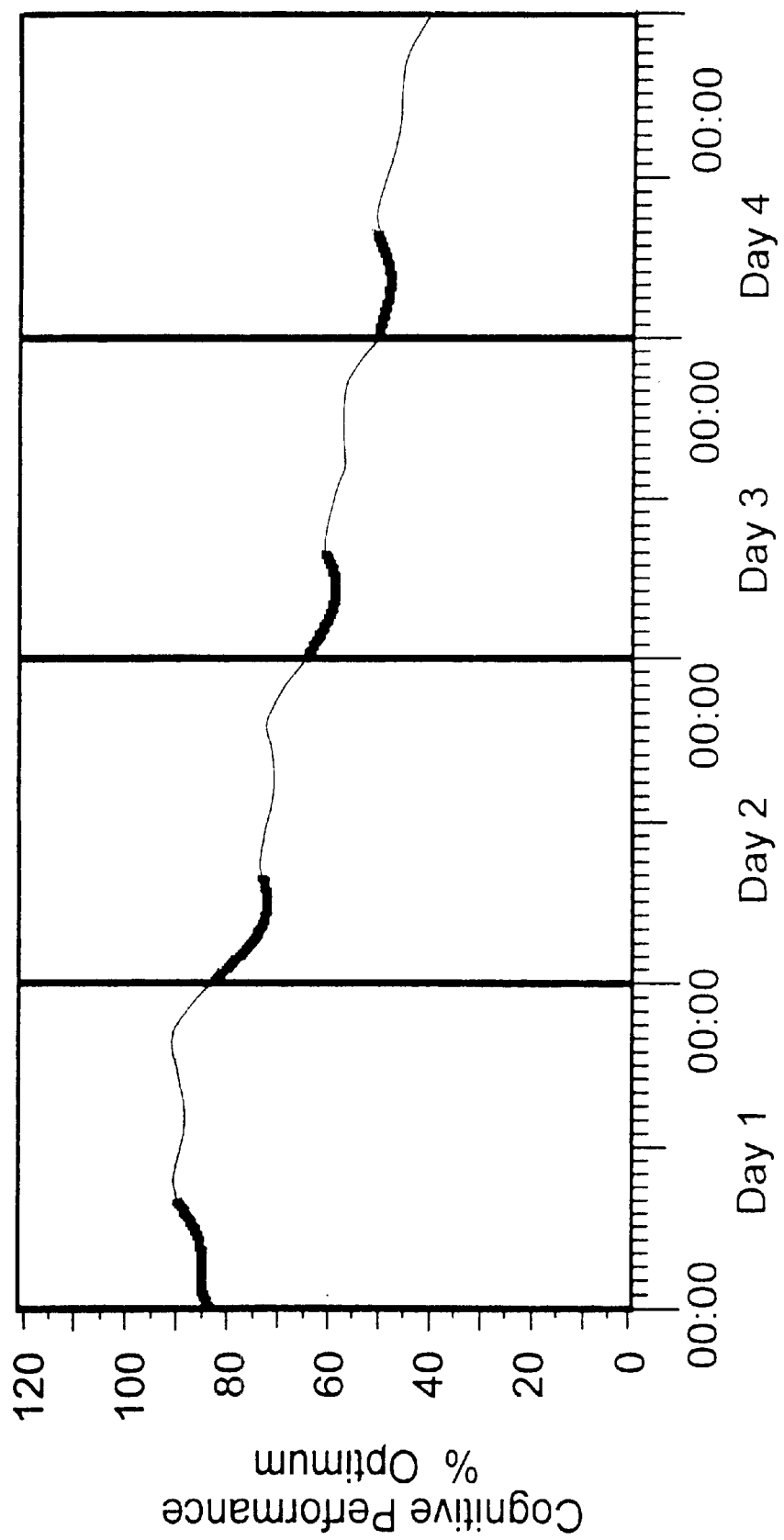
FIG. 13 illustrates predicted cognitive performance with sleep fragmented with 10 arousals per hour.

Another practical application uses the method to predict the cognitive performance in an individual with fragmented sleep, either due to a sleep disorder such as sleep apnea or due to environmental disturbances such as airplane or train noises. FIG. 13 illustrates predicted cognitive performance E across three nights of fragmented sleep, during which arousals (brief awakenings) occur 10 times per hour. Daytime predicted cognitive performance E following nights on Days 2–4 (when sleep is disturbed) is severely impaired, and continues to decline across each day. Predicted cognitive performance E will not be completely restored even after one night of eight hours of undisturbed sleep.

(3) Predicted Cognitive Performance E across Two Night Shifts

Figure 14:
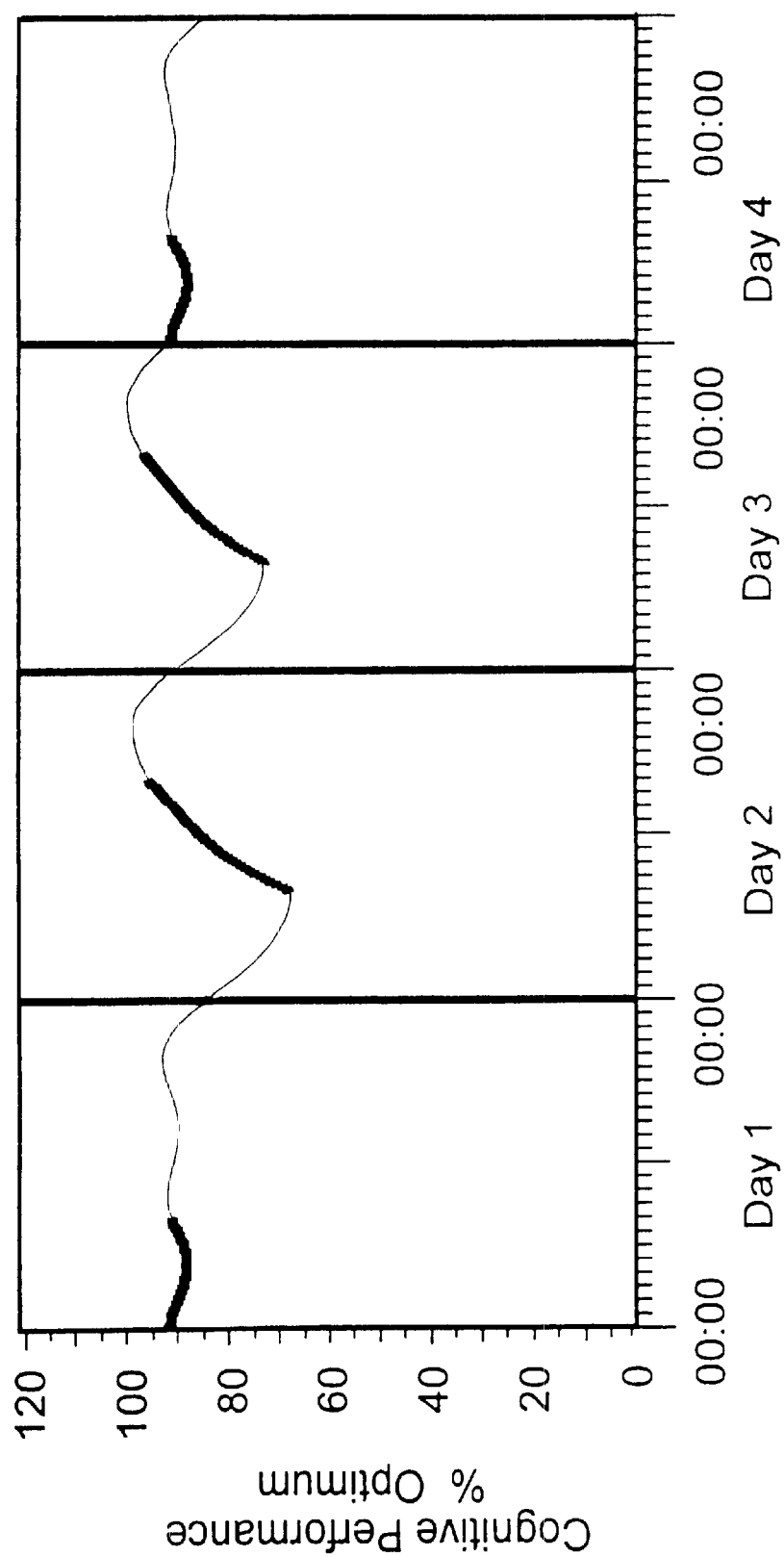
FIG. 14 illustrates predicted cognitive performance for two nights of shift work with daytime sleep.

Another practical application uses the method to predict the cognitive performance E of an individual across two nights of shift work. FIG. 14 illustrates predicted cognitive performance E across two nights during which the individual works from 11:00 PM to 7:00 AM and sleeps from 8:00 AM to 4:00 PM. Prior to the first shift, the individual sleeps his usual day-shift hours, i.e., from midnight to 8:00 AM. He stays up all day and starts his first shift at 11:30 PM that night. The shaded area shows that he is working when predicted cognitive performance E is poorest for that 24-hour period. This is due to the combined influences of sleep deprivation and time of day. The person then sleeps from 8:00 AM to 4:00 PM—for the purposes of this exercise, it is assumed that the person actually slept the entire eight hours of this latter sleep period. Substantial recovery of predicted cognitive performance E is obtained during this sleep period. The second shift begins with predicted cognitive performance E at near-optimal levels. However, due to time of day effects, the bulk of the second shift occurs when the method predicts poorest cognitive performance E.

(4) Retrospective Analysis of Predicted Cognitive Performance E

Figure 15:
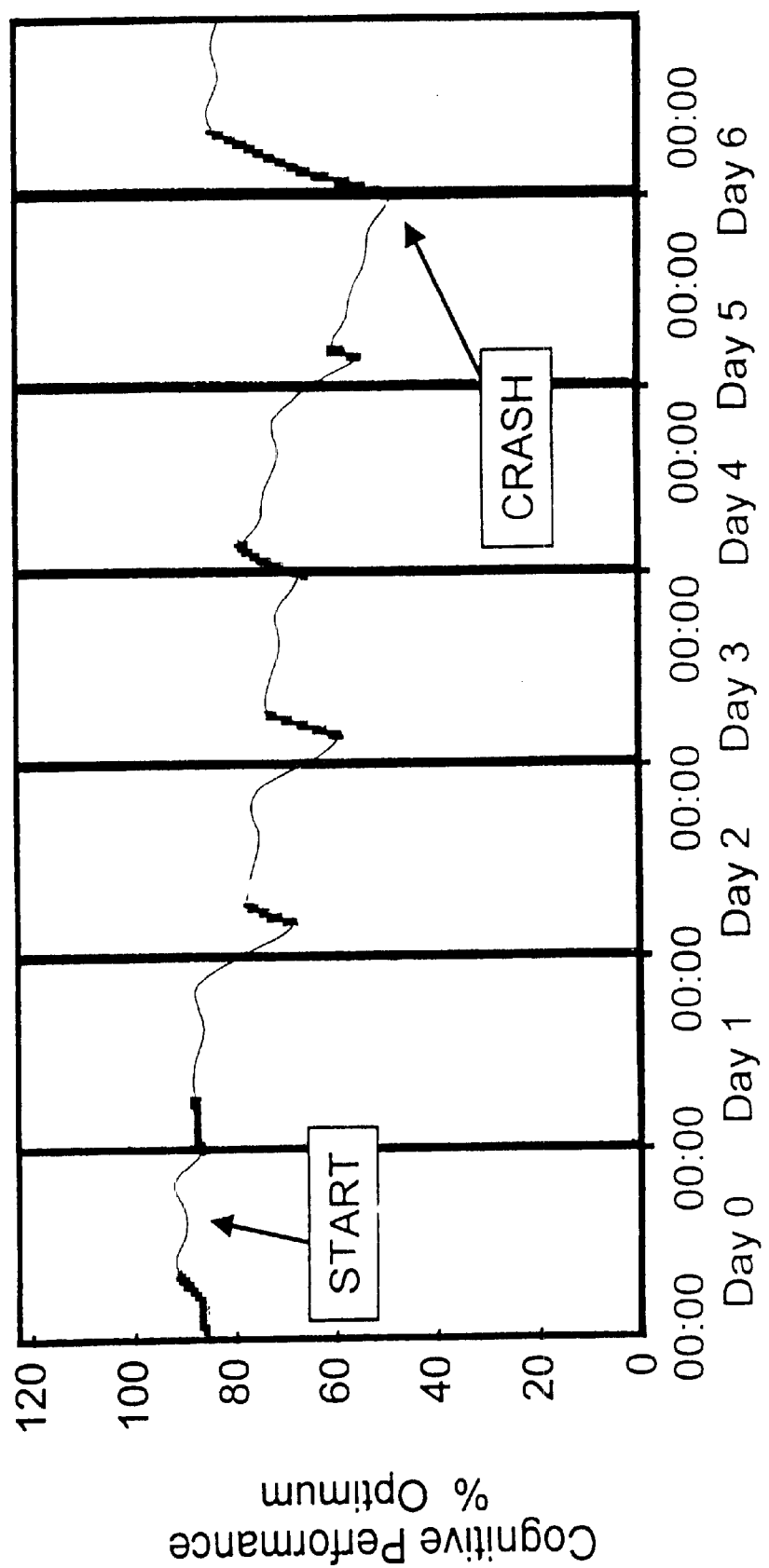
FIG. 15 illustrates predicted cognitive performance prior to a commercial vehicle driver collision.

In another application, the method is used to retrospectively predict cognitive performance E in a commercial motor vehicle operator involved in a driving collision/traffic accident. The driver's approximate sleep and wake times (taken from personal history) for several days prior to the collision serve as input. Predicted cognitive performance E based on this approximate sleep/wake data is depicted in FIG. 15. The driver's trip began the morning of Day 1. Due to an early start time, the driver began the trip partially sleep deprived. Consequently, his predicted cognitive performance E at the start of the trip was only slightly above the arbitrarily defined acceptable level of 85%. During the first day (Day 1) on the road, the driver worked for 16 hours— predicted cognitive performance E during the latter portion of this period fell below acceptable levels. The driver stopped for his first sleep at 4:00 AM on Day 2. Sleep on Days 2–4 was of insufficient duration to restore predicted cognitive performance E. On Day 5, the driver obtained little sleep (30 minutes). The collision occurred later that day as the driver's predicted cognitive performance E began the rapid evening decline. At the time of the collision, the driver's predicted cognitive performance E was approximately 50% of optimal levels. Finally, given the extreme sleep deprivation, the predicted cognitive performance recovery slope during sleep on Day 6 (following the collision) was steep, restoring predicted cognitive performance E to near the arbitrary 85% "acceptable" level.

(5) Predicted Cognitive Performance E Based on Current Sleep/Wake Schedule and Modification of Future Sleep/Wake to Optimize Predicted Cognitive Performance E In this application, the method is used first to predict an individual's level of cognitive performance E across some interval based on that individual's current work and sleep/wake schedule. Next, the method is used to re-schedule sleep and wakefulness in order to optimize predicted cognitive performance E over the same interval.

Figure 16:
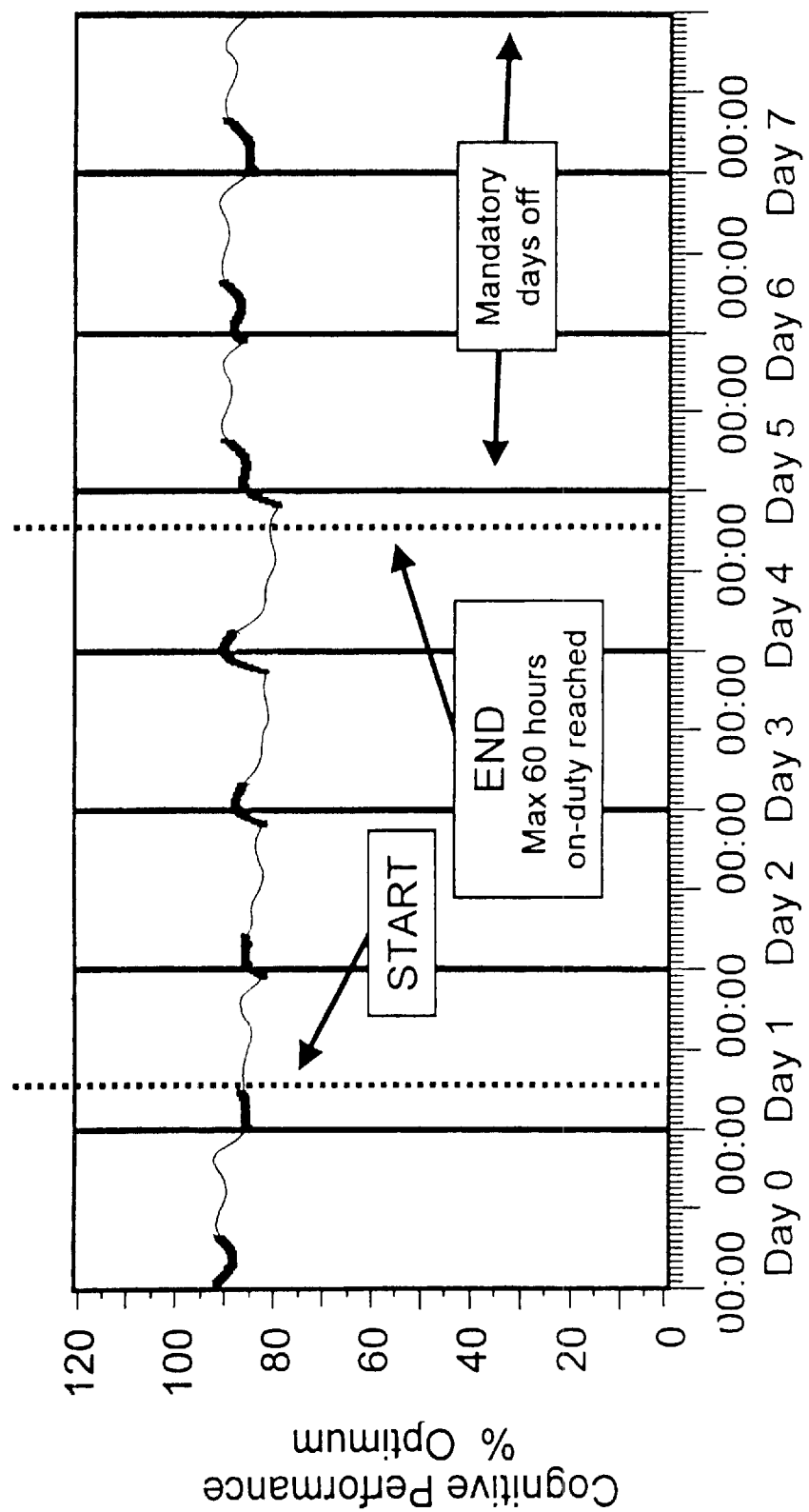
FIG. 16 illustrates predicted cognitive performance with 15 hours on-duty/8 hours off-duty schedule with 6 hours sleep per night during duty days.

In this example, first we model a driver's predicted cognitive performance E based on his current sleep/wake schedule. The driver's current sleep/wake schedule is generated around the maximum duty hours allowed under the Federal Highway Administration's (FHWA) hours-of-service regulations. These regulations allow the driver to obtain a maximum 15 hours on-duty (maximum 10 hours driving plus five hours on-duty but not driving) followed by a minimum eight hours off-duty. The driver may continue this on/off-duty cycling until 60 hours on-duty has been accumulated—at which point the driver must take time off until seven days has elapsed since he commenced duty. FIG. 16 illustrates the driver's sleep/wake schedule and predicted cognitive performance E under these restrictions. The driver sleeps six of his eight hours off-duty. The schedule results in a 23-hour "day" which means that the driver initiates sleep one hour earlier each evening. Because partial sleep deprivation occurs and sleep is timed earlier each day, the invention predicts that by the second duty day the driver will spend a substantial portion of on-duty time with predicted cognitive performance E below the arbitrarily defined 85% cut-off. When the driver reaches the maximum 60 hours on-duty, he must then take several days off even though the invention predicts that cognitive performance E is restored after only one night of 10 hours sleep.

Figure 17:
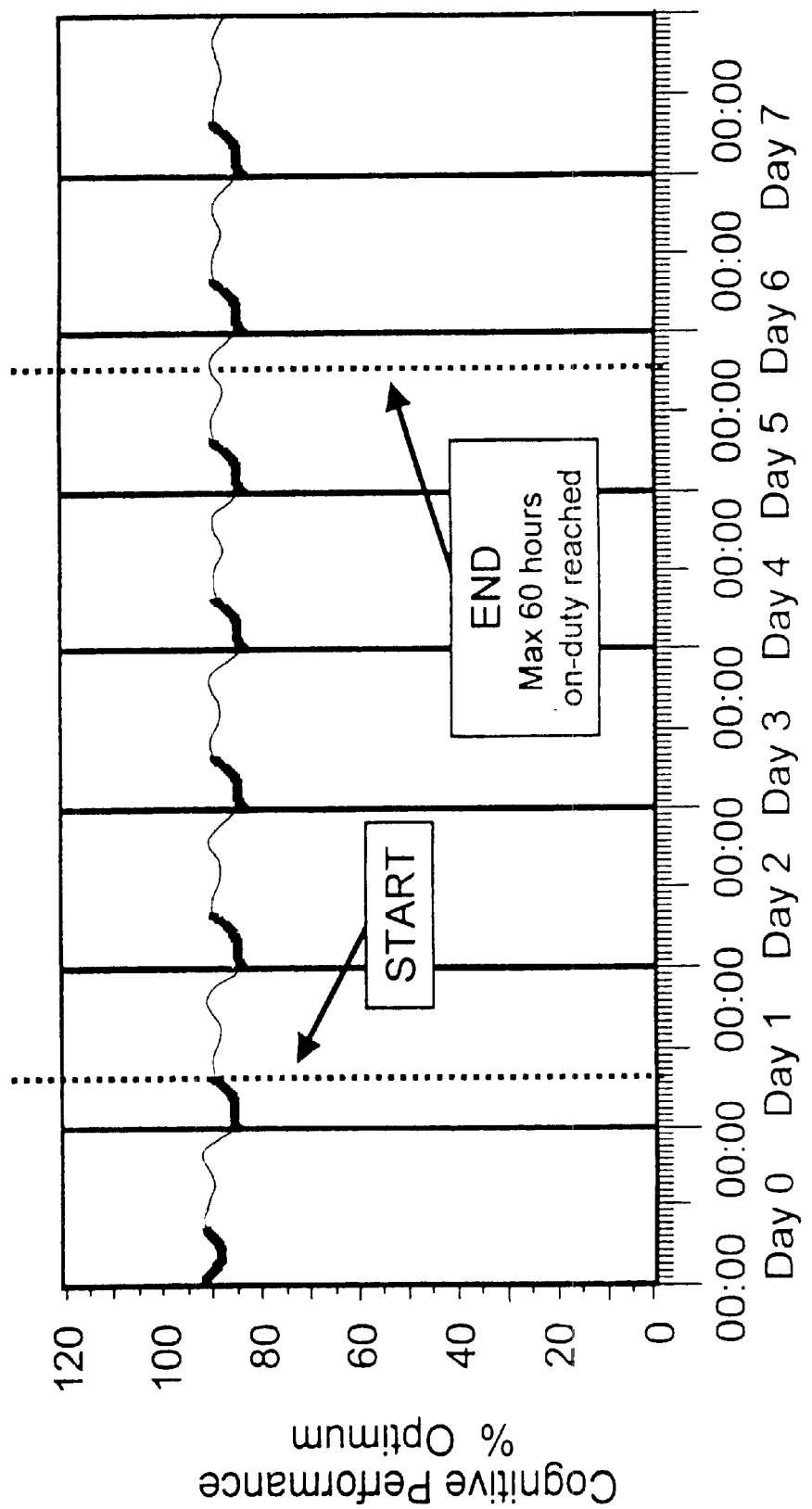
FIG. 17 illustrates predicted cognitive performance with alternative 12 hours on-duty/12 hours off-duty schedule with 8 hours sleep per night during duty days.

FIG. 17 illustrates an alternative work schedule also allowed under current FHWA regulations. This work schedule is based on a schedule of 12 hours on-duty and 12 hours off-duty. It is assumed that the driver sleeps eight of his 12 hours off-duty. Because no sleep deprivation or shifting of sleep timing occurs, the invention predicts that the driver maintains cognitive performance E at or above 85% within and across the duty days.

INDUSTRIAL APPLICABILITY

Although described above in connection with a variety of specific activities, this invention has many other applications. The method for predicting cognitive performance will provide critical information for managing both individual and group productivity. For example, in military operational planning, this method will enable commanders to determine precisely, based on prior sleep history, each soldier's current and predicted level of cognitive performance. Commanders can also input a likely sleep/wake schedule and thereby predict a soldier's cognitive performance throughout an impending mission. Throughout conduct of the mission itself, the latter cognitive performance predictions (originally based on likely sleep/wake schedule) can be updated based on actual sleep acquired. The ability to project future cognitive performance will allow commanders to optimize troop performance during continuous operations by, for example, planning sleep/wake schedules around the mission to optimize cognitive performance, selecting those troops or combinations of troops whose predicted cognitive performance will be maximal at a critical time, etc. This method will assist in maximizing productivity at both the individual and unit level.

This invention may be employed in a variety of commercial applications covering many occupational areas for purposes of optimizing output (productivity). The invention provides managers with the capability to plan operations and regulate work hours to a standard based on objective cognitive performance predictions. This is in contrast to the frequently used method of regulating work hours by time off-duty (a relatively poor predictor of sleep/wake patterns and consequently a poor predictor of cognitive performance) or by generating alertness/sleepiness predictions (which, as noted above, do not always correspond to cognitive performance). The invention can be "exercised" in hypothetical sleep/wake scenarios to provide an estimate of cognitive performance under such scenarios. To the extent that optimizing cognitive performance is of interest to the general public, there is a possibility for use in a variety of applications.

The method may also be used to gauge and evaluate the cognitive performance effects of any biomedical, psychological, or other (e.g., sleep hygiene, light therapy, etc.) treatments or interventions shown to improve sleep. Examples of these include but are not limited to patients with overt sleep disorders, circadian rhythm disorders, other medical conditions impacting sleep quality and/or duration, poor sleep hygiene, jet lag, or any other sleep/wake problem. Currently, the efficacy of treatments for improving sleep is determined by comparing baseline polysomnographic measures of nighttime sleep and some measure of daytime alertness (e.g., the MSLT, the Maintenance of Wakefulness Test (MWT), the Stanford Sleepiness Scale or the Karolinska Sleepiness Scale) with the same measures obtained after treatment. Both treatment efficacy and the likely impact on performance during waking periods are inferred from the results on the daytime alertness tests. For example, the Federal Aviation Administration currently requires any commercial pilots diagnosed with sleep apnea to undergo treatment. Such treatment is followed by daytime alertness testing on a modified version of the MWT. During the MWT, pilots are put in a comfortable chair in a darkened room and instructed to try to remain awake for extended periods. If the pilots are able to avoid overt sleep under these sleep-conducive conditions then they are deemed fit for duty. The inference is that the minimal ability to maintain wakefulness at a discrete point in time translates into the ability to operate an aircraft safely (i.e., it is inferred that alertness is equivalent to cognitive performance). However, sleep deprivation can affect cognitive performance even when it does not result in overt sleep, particularly during an alertness test when for various reasons the individual may be highly motivated to stay awake.

In contrast, the current method allows cognitive performance to be estimated directly from measured sleep parameters considered in conjunction with the time of day. The advantages of this method over current methods for evaluating treatment efficacy are: (1) the motivations and motivation levels of the patients being tested cannot affect results (cognitive performance determinations); and (2) the method allows numerical specification and prediction of cognitive performance across all projected waking hours rather than indicating alertness at a discrete, specified point in time. Thus, the method provides a continuous scale for gauging cognitive performance across time rather than providing only a minimal "fitness for duty" determination based on the patient's ability to maintain EEG-defined wakefulness at a specific time.

The method may also be used clinically as an adjunct for diagnosing sleep disorders such as narcolepsy and idiopathic CNS hypersomnolence. Equally important, it may also be used to differentiate among sleep disorders. The latter is critical to the course of treatment, and consequent treatment efficacy depends on a valid and reliable diagnosis. For example, sleep apnea and periodic limb movements during sleep are characterized by nighttime sleep disruption (i.e., partial sleep deprivation) accompanied by daytime cognitive performance deficits. In contrast, narcolepsy and idiopathic hypersomnolence tend to be characterized by apparently normal nighttime sleep, but accompanied by daytime cognitive performance deficits. Based on the apparently normal nighttime sleep in the latter two groups, the invention would predict relatively normal cognitive performance. Thus, a discrepancy between predicted cognitive performance (based on the current invention) and observed or measured cognitive performance could be used to distinguish one sleep disorder from another. For example, narcolepsy, idiopathic hypersomnolence, or other CNS-related causes of daytime cognitive performance deficits (where no sleep deficit is apparent) could be distinguished from sleep apnea, periodic limb movements, or other causes of daytime cognitive deficits (where impaired sleep is evident).

Those skilled in the art will appreciate that various adaptations and modifications of the above-described preferred embodiments can be configured without departing from the scope and spirit of the invention. Therefore, it is to be understood that, within the scope of the appended claims, the invention may be practiced other than as specifically described herein.

We claim:

1. A method for determining a predicted cognitive performance level comprising:
   a. inputting a data series having wake states and sleep states of an individual,
   b. selecting a function based on the wake states and sleep states in the data series,
   c. calculating a cognitive performance capacity based on the selected function,
   d. modulating the cognitive performance capacity with a time of day value,
   e. outputting the modulated value as the predicted cognitive performance, and
   when a piece of data within the data series is inconclusive, then
      selecting at least two functions,
      determining a cognitive performance capacity using each function,
      modulating each cognitive performance capacity with a time of day value,
      providing each modulated value, and
      repeating the steps a through e for each modulated value at least once.

2. The method according to claim 1 further comprising:
   storing the modulated values,
   repeating steps b through e,
   plotting a curve from the stored modulated values, and
   outputting the curve representing cognitive performance level over time.

3. The method according to claim 2, wherein the data series includes past information such that the curve is used to determine the cognitive level of an individual at an earlier time.

4. The method according to claim 2, further comprising extrapolating from the curve a predictive curve based on anticipated wake states and anticipated sleep states.

5. The method according to claim 1, wherein said outputting step includes outputting the predicted cognitive performance to a display.

6. The method according to claim 1, wherein said outputting step includes outputting the predicted cognitive performance to a data file.

7. The method according to claim 1, wherein said outputting step includes outputting the predicted cognitive performance to a printing device.

8. The method according to claim 1, further comprising formulating the time of day values to represent a curve having a period of 24 hours.

9. The method according to claim 8, wherein the curve includes a first sinusoidal curve having a 24-hour period and a second sinusoidal curve having a 12-hour period.

10. The method according to claim 1, wherein the time of day values represent a curve having a period of 24 hours.

11. The method according to claim 10, wherein the curve includes a first sinusoidal curve having a 24-hour period and a second sinusoidal curve having a 12-hour period.

12. The method according to claim 1, wherein the data series is obtained from a device adapted to be attached to the individual.

13. The method according to claim 1, wherein the data series is an output of a sleep scoring system.

14. The method according to claim 1, wherein step a includes selecting from a group consisting of a wake function, a sleep function, a delay function, and a sleep inertia function.

15. The method according to claim 1, wherein step a includes selecting from a group consisting of a wake function, a sleep function, and a sleep inertia function.

16. The method according to claim 1, wherein step a includes
   determining a present state for the data series as either a wake state or a sleep state,
   calculating a length of time in the present state, and
   selecting the function based on the length of time in the present state and the present state.

17. The method according to claim 16, wherein the selecting the function step selects from a group consisting of a wake function, a sleep function, a delay function, and a sleep inertia function.

18. The method according to claim 1, wherein when another inconclusive piece of data is found, then the selecting a function includes determining the two functions that would provide the lowest cognitive performance capacity and the highest cognitive performance capacity among the combinations of cognitive performance capacities resulting from the inconclusive pieces of data.

19. The method according to claim 1, wherein the first calculating step calculates a cognitive performance level as a percentage value such that 100% is a maximum cognitive performance capacity.

20. The method according to claim 1, wherein said method is performed in real-time.

21. A computer data signal embodied in a carrier wave readable by a computing system and encoding a computer program of instructions for executing a computer process performing a method for determining a cognitive performance level comprising:
   inputting a data series having wake states and sleep states of an individual,
   selecting a function based on the wake states and sleep states in the data series,
   calculating a cognitive performance capacity based on the selected function,
   modulating the cognitive performance capacity with a time of day value, and
   outputting the modulated value as the predicted cognitive performance.

22. A computer-readable medium having computer-executable instructions for a method for determining a cognitive performance level comprising:
   inputting a data series having wake states and sleep states of an individual,
   selecting a function based on the wake states and sleep states in the data series,
   calculating a cognitive performance capacity based on the selected function,
   modulating the cognitive performance capacity with a time of day value, and
   outputting the modulated value as the predicted cognitive performance.

23. A method for determining a predicted cognitive performance comprising:
   inputting a data series having wake states and sleep states of an individual,
   selecting a function based on the wake states and sleep states in the data series,
   calculating a cognitive performance capacity based on the selected function,
   approximating a first curve of calculated cognitive performance capacities,
   modulating the first curve with a second curve representing time of day rhythms, and
   outputting the modulated first curve representing the predicted cognitive performance; and
   wherein the data series includes past wake states and past sleep states such that the modulated first curve is used to determine the cognitive level of an individual at an earlier time.

24. The method according to claim 23, wherein said outputting step includes outputting a value of a point on the modulated first curve to a display.

25. The method according to claim 23, wherein said outputting step includes outputting a value of a point on the modulated first curve to a data file.

26. The method according to claim 23, wherein said outputting step includes outputting a value of a point on the modulated first curve to a printing device.

27. The method according to claim 23, further comprising extrapolating from the modulated first curve a predictive curve based on anticipated wake states and anticipated sleep states.

28. The method according to claim 23, further comprising formulating the second curve having a period of 24 hours such that the second curve includes a first sinusoidal curve having a 24-hour period and a second sinusoidal curve having a 12-hour period.

29. The method according to claim 23, wherein the second curve has a period of 24 hours such that the second curve includes a first sinusoidal curve having a 24-hour period and a second sinusoidal curve having a 12-hour period.

30. The method ,according to claim 23, wherein the data series is obtained from a device adapted to be attached to the individual.

31. The method according to claim 23, wherein the data series is an output of a sleep scoring system.

32. The method according to claim 23, wherein the selecting step selects from a group consisting of a wake function, a sleep function, a delay function, and a sleep inertia function.

33. The method according to claim 23, wherein the selecting step includes:
   determining a present state for the data series as either the wake state or the sleep state,
   calculating a length of time in the present state, and
   selecting the function based on the length of time in the present state and the present state.

34. The method according to claim 33, wherein the selecting the function step selects from a group consisting of a wake function, a sleep function, a delay function, and a sleep inertia function.

35. The method according to claim 23, wherein the calculating step includes calculating a cognitive performance level as a percentage value such that 100% is a maximum cognitive performance capacity.

36. The method according to claim 23, wherein said method operates in real-time.

37. A computer data signal embodied in a carrier wave readable by a computing system and encoding a computer program of instructions for executing a computer process performing a method for determining a predicted cognitive performance comprising:
   inputting a data series having wake states and sleep states of an individual,
   selecting a function based on the wake states and sleep states in the data series,
   calculating a cognitive performance capacity based on the selected function,
   approximating a first curve of calculated-cognitive performance capacities,
   modulating the first curve with a second curve representing time of day rhythms, and
   outputting the modulated first curve representing the predicted cognitive performance.

38. A computer-readable medium having computer-executable instructions for a method for determining a predicted cognitive performance comprising:
   inputting a data series having wake states and sleep states of an individual,
   selecting a function based on the wake states and sleep states in the data series,
   calculating a cognitive performance capacity based on the selected function,
   approximating a first curve of calculated cognitive performance capacities,
   modulating the first curve with a second curve representing time of day rhythms, and
   outputting the modulated first curve representing the predicted cognitive performance.

39. An apparatus comprising:
   input means for receiving data,
   interpretation means for analyzing the received data and selecting a calculation function based on the composition of the received data,
   determination means for calculating a cognitive performance capacity using the selected calculation function,
   storing means for storing modulation data, and
   modulating means for modulating the cognitive performance capacity with modulation data to produce a predicted cognitive performance.

40. The apparatus of claim 39, further comprising a means for displaying the predicted cognitive performance.

41. The apparatus of claim 39, wherein said interpretation means includes means for sleep scoring the received data.

42. The apparatus of claim 39, wherein said interpretation means determines a time representing a length of time of a current state of the data.

43. The apparatus of claim 39, wherein said interpretation means determines a time representing a transition from one state to another.

44. The apparatus of claim 39, wherein the modulating on data represents variations over a 24-hour period.

45. The apparatus of claim 39, wherein said modulating means time sequences the cognitive performance capacity with the modulation data.

46. The apparatus of claim 39, further comprising storage means for storing the predicted cognitive performance from said modulating means.

47. The apparatus of claim 46, wherein said storage means stores the predicted cognitive performance as a series of data.

48. The apparatus of claim 39, further comprising means for communicating at least one of the cognitive performance capacity from said determination means and the predicted cognitive performance from said modulating means to a central device.

49. The apparatus of claim 48, wherein said communicating means communicates using telemetry.

50. A computer readable material having program code embodied therein for generating a predictive cognitive performance level measure based on a sleep/wake history of an individual, said material comprising:
   means for analyzing sleep/wake input data and selecting a function based on the analysis,
   means for calculating a cognitive performance capacity based on the sleep/wake input data and the selected function,
   means for modifying the calculated cognitive performance capacity based on stored data, and
   means for outputting the modified cognitive performance capacity as a predicted cognitive performance level.

51. The computer readable material according to claim 50, wherein means for modifying includes means for matching of the stored data with the cognitive performance capacity based on temporal data connected to the input sleep/wake data.

* * * * *

UNITED STATES PATENT AND TRADEMARK OFFICE
CERTIFICATE OF CORRECTION

PATENT NO. : 6,553,252 B2
DATED : April 22, 2003
INVENTOR(S) : Balkin et al.

It is certified that error appears in the above-identified patent and that said Letters Patent is hereby corrected as shown below:

Column 31,
Lines 44-50, claim 18 should read:
-- The method according to claim 1, wherein when another inconclusive piece of data is found, then the selecting at least two functions includes determining the two functions that would provide the lowest cognitive performance capacity and the highest cognitive performance capacity among the combinations of cognitive performance capacities resulting from the inconclusive pieces of data. --

Column 34,
Lines 18 and 19, claim 44 should read:
-- The apparatus of claim 39, wherein the modulating data represents variations over a 24-hour period. --

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,553,252 B2
DATED : April 22, 2003
INVENTOR(S) : Balkin et al.

It is certified that error appears in the above-identified patent and that said Letters Patent is hereby corrected as shown below:

Column 32,
Line 58, after "method" and before "according", remove ","

Signed and Sealed this

Twenty-seventh Day of July, 2004

JON W. DUDAS
*Acting Director of the United States Patent and Trademark Office*